US008637498B2

(12) United States Patent
Connolly et al.

(10) Patent No.: US 8,637,498 B2
(45) Date of Patent: Jan. 28, 2014

(54) OXOPIPERAZINE-AZETIDINE AMIDES AND OXODIAZEPINE-AZETIDINE AMIDES AS MONOACYLGLYCEROL LIPASE INHIBITORS

(75) Inventors: Peter J. Connolly, New Providence, NJ (US); Mark J. Macielag, Branchburg, NJ (US); Mark E. McDonnell, Lansdale, PA (US); Bin Zhu, Hillsborough, NJ (US)

(73) Assignee: Janssen Pharmaceutica, NV, Beerse (BE)

( * ) Notice: Subject to any disclaimer, the term of this patent is extended or adjusted under 35 U.S.C. 154(b) by 182 days.

(21) Appl. No.: 13/246,232

(22) Filed: Sep. 27, 2011

(65) Prior Publication Data

US 2012/0077797 A1    Mar. 29, 2012

Related U.S. Application Data

(60) Provisional application No. 61/386,777, filed on Sep. 27, 2010.

(51) Int. Cl.
| | | |
|---|---|---|
| *A61K 31/496* | (2006.01) | |
| *A61K 31/506* | (2006.01) | |
| *A61K 31/551* | (2006.01) | |
| *C07D 403/04* | (2006.01) | |
| *C07D 403/14* | (2006.01) | |
| *C07D 409/14* | (2006.01) | |
| *C07D 417/14* | (2006.01) | |

(52) U.S. Cl.
USPC ...... 514/210.18; 514/218; 540/575; 544/295; 544/359; 544/368; 544/369; 544/371; 544/373; 544/376

(58) Field of Classification Search
None
See application file for complete search history.

(56) References Cited

U.S. PATENT DOCUMENTS

| 8,399,454 B2* | 3/2013 | Bian et al. ............... 514/217.05 |
| 8,415,341 B2* | 4/2013 | Chevalier et al. ........ 514/210.18 |
| 8,435,977 B2* | 5/2013 | Flores et al. ............. 514/210.18 |
| 2004/0167224 A1 | 8/2004 | Ozaki et al. |
| 2006/0148844 A1 | 7/2006 | Nakade et al. |
| 2007/0142394 A1 | 6/2007 | Solomon et al. |
| 2007/0293496 A1 | 12/2007 | Ozaki et al. |
| 2009/0269785 A1 | 10/2009 | Schubert et al. |
| 2010/0041651 A1 | 2/2010 | Even et al. |

FOREIGN PATENT DOCUMENTS

| FR | 2915199 A1 | 10/2008 |
| WO | 98/37077 A1 | 8/1998 |
| WO | 99/19297 A1 | 4/1999 |
| WO | 00/63168 A1 | 10/2000 |
| WO | 01/77101 A1 | 10/2001 |
| WO | 2004/056800 A1 | 7/2004 |
| WO | 2006/097175 A1 | 9/2006 |
| WO | 2008/145842 A2 | 12/2008 |
| WO | 2008/145843 A1 | 12/2008 |
| WO | 2009/117444 A1 | 9/2009 |
| WO | 2009/132267 A1 | 10/2009 |
| WO | 2010/124082 A1 | 10/2010 |
| WO | 2010/124108 A1 | 10/2010 |
| WO | 2010/124121 A1 | 10/2010 |

OTHER PUBLICATIONS

PCT counterpart to U.S. Appl. No. 12/765,617, International Search Report and Written Opinion, PCT/US2010/032098, dated Jun. 18, 2010.
International Preliminary Report, PCT/US2010/032098, dated Oct. 25, 2011.
PCT counterpart to U.S. Appl. No. 12/765,675, International Search Report and Written Opinion, PCT/US2010/032100, dated Jun. 15, 2010.
International Preliminary Report, PCT/US2010/032100, dated Oct. 25, 2011.
PCT counterpart to U.S. Appl. No. 13/224,654, International Search Report and Written Opinion, PCT/US2011/049885, dated Oct. 11, 2011.
International Preliminary Report, PCT/US2011/049885, dated Mar. 5, 2013.
PCT counterpart to U.S. Appl. No. 13/246,232, International Search Report and Written Opinion, PCT/US2011/053442, dated Jan. 10, 2012.
International Preliminary Report, PCT/US2011/053442, dated Apr. 2, 2013.

(Continued)

*Primary Examiner* — Emily Bernhardt
(74) *Attorney, Agent, or Firm* — Thomas J. Dodd

(57) ABSTRACT

Disclosed are compounds, compositions and methods for treating various diseases, syndromes, conditions and disorders, including pain. Such compounds, and enantiomers, diastereomers, and pharmaceutically acceptable salts thereof, are represented by Formula (Ia) and Formula (Ib) as follows:

Formula (Ia)

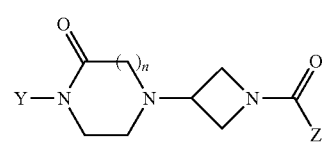

wherein Y, Z, and n are defined herein; and

Formula (Ib)

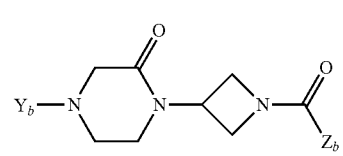

wherein $Y_b$ and $Z_b$ are as defined herein.

30 Claims, No Drawings

(56) References Cited

OTHER PUBLICATIONS

PCT counterpart to U.S. Appl. No. 13/277,734, International Search Report and Written Opinion, PCT/US2011/057090, dated Jan. 27, 2012.
International Preliminary Report, PCT/US2011/057090, dated Apr. 23, 2013.
PCT counterpart to U.S. Appl. No. 13/277,702, International Search Report and Written Opinion, PCT/US2011/057085, dated Jan. 27, 2012.
International Preliminary Report, PCT/US2011/057085, dated Apr. 23, 2013.
PCT counterpart to U.S. Appl. No. 13/628,331, International Search Report and Written Opinion, PCT/US2012/057461, dated Dec. 4, 2012.
PCT counterpart to U.S. Appl. No. 13/628,428, International Search Report and Written Opinion, PCT/US2012/057465, dated Dec. 12, 2012.
PCT counterpart to U.S. Appl. No. 13/628,452, International Search Report and Written Opinion, PCT/US2012/057470, dated Dec. 3, 2012.
PCT counterpart to U.S. Appl. No. 12/765,018, International Search Report and Written Opinion, PCT/US2010/032045, dated Jun. 11, 2010, 12 pages.
PCT counterpart to U.S. Appl. No. 12/765,048, International Search Report and Written Opinion, PCT/US2010/032049, dated Jun. 15, 2010, 12 pages.
PCT counterpart to USSN: 12/12/765076. International Search Report and Written Opinion, PCT/US2010/032068, dated Jun. 14, 2010, 12 pages.
PCT counterpart to U.S. Appl. No. 12/765,103, International Search Report and Written Opinion, PCT/US2010/032082, dated Jun. 15, 2010, 12 pages.
PCT counterpart to U.S. Appl. No. 12/765,179, International Search Report and Written Opinion, PCT/US2010/032086, dated Jun. 14, 2010, 12 pages.
PCT counterpart to U.S. Appl. No. 12/765,254, International Search Report and Written Opinion, PCT/US2010/032089, dated Jun. 14, 2010, 12 pages.
PCT counterpart to U.S. Appl. No. 12/765,420, International Search Report and Written Opinion, PCT/US2010/032092, dated Jun. 15, 2010, 12 pages.
PCT counterpart to U.S. Appl. No. 12/765,487, International Search Report and Written Opinion, PCT/US2010/032095, dated Jun. 14, 2010, 12 pages.
Ben-Shabat et al., "An entourage effect: inactive endogenous fatty acid glycerol esters enhance 2-arachidonoyl-glycerol cannabinoid activity", Eur J Pharmacol, 1998, vol. 353, pp. 23-31.
Benito et al., "Cannabinoid CB2 receptors in human brain inflammation", Brit J Pharmacol, 2008, vol. 153, pp. 277-285.
Bennett et al., "A peripheral mononeuropathy in rat that produces disorders of pain sensation like those seen in man.", Pain, 1988, vol. 33(1), pp. 87-107.
Cavuoto et al., "The expression of receptors for endocannabinoids in human and rodent skeletal muscle", Biochem Biophys Res Commun, 2007, vol. 364, pp. 105-110.
Chaplan et al., "Quantitative assessment of tactile allodynia in the rat paw", J. Neurosci Methods, 1994, vol. 53(1), pp. 55-63.
Comelli et al., "The inhibition of monoacylglycerol lipase by URB602 showed an anti-inflammatory and anti-nociceptive effect in a murine model of acute inflammation", Brit J Pharmacol, 2007, vol. 152, pp. 787-794.
Cravatt et al., "The Endogenous Cannabinoid System and Its Role in Nociceptive Behavior", J Neurobiol, 2004, vol. 61, pp. 149-160.
Database Registry [Online] Chemical Abstracts Service, Columbus, OH, US; Nov. 3, 2010.

Devane et al., "Isolation and Structure of a Brain Constituent That Binds to the Cannabinoid Receptor", Science, 1992, vol. 258, pp. 1946-1949.
Di Marzo et al., "Endocannabinoids: New Targets for Drug Development", Curr Pharm Des, 2000, vol. 6, pp. 1361-1380.
Di Marzo et al., "Endocannabinoids and the Regulation of their levels in Health and Disease", Curr Opin Lipidol, 2007, vol. 18, pp. 129-140.
Dogrul et al., "'Knock-down' of spinal CB1 receptors produces abnormal pain and elevates spinal dynorphin content in mice", Pain, 2002, vol. 100, pp. 203-209.
Dixon, W. J., "Efficient analysis of experimental observations", Annu. Rev. Pharmacol. Toxicol., 1980, vol. 20, pp. 441-462.
Guindon et al., "Cannabinoid CB2 receptors: a therapeutic target for the treatment of inflammatory and neuropathic pain", Brit J Pharmacol, 2008, vol. 153, pp. 319-334.
Hajrasouliha et al., "Endogenous cannabinoids contribute to remote ischemic preconditioning via cannabinoid CB2 receptors in the rat heart", Eur J Pharmacol, 2008, vol. 579, pp. 246-252.
Jhaveri et al., "Endocannabinoid metabolism and uptake: novel targets for neuropathic and inflammatory pain", Brit J Pharmacol, 2007, vol. 152, pp. 624-632.
Kathuria et al., "Modulation of anxiety through blockade of anandamide hydrolysis", Nat Med, 2003, vol. 9, pp. 76-81.
Lichtman et al., "Mice lacking fatty acid amide hydrolase exhibit a cannabinoid receptor-mediated phenotypic hypoalgesia", Pain, 2004, vol. 109, pp. 319-327.
Lichtman et al., "Pharmacological Activity of Fatty Acid Amides Is Regulated, but Not Mediated, by Fatty Acid Amide Hydrolase in Vivo", J Pharmacol Exp Ther, 2002, 302, pp. 73-79.
Matsuda et al., "Structure of a Cannabinoid Receptor and Functional Expression of the cloned cDNA", Nature, 1990, vol. 346, pp. 561-564.
Matulis et al., "Thermodynamic Stability of Carbonic Anhydrase: Measurements of Binding Affinity and Stoichiometry Using ThermoFluor.", Biochemistry, 2005, vol. 44, pp. 5258-5266.
McCarberg B. et al., "The Future of Cannabinoids as Analgesic Agents: A Pharmacologic, Pharmacokinetic, and Pharmacodynamic Overview", Amer J Ther, 2007, vol. 14, pp. 475-83.
Mechoulam et al., "Identification of an Endogenous 2-Monoglyceride, Present in Canine Gut, that Binds to Cannabinoid Receptors", Biochem Pharmacol, 1995, vol. 50, pp. 83-90.
Munro et al., "Molecular Characterization of a Peripheral Receptor for Cannabinoids", Nature, 1993, vol. 365, pp. 61-65.
Njie, Ya Fatou et al, "Aqueous humor outflow effects of 2-arachidonylglycerol", Exp. Eye Res., 2008, vol. 87(2), pp. 106-114.
Pacher et al., "Pleiotropic effects of the CB2 cannabinoid receptor activation on human monocyte migration: implications for atherosclerosis and inflammatory diseases", Amer J Physiol, 2008, vol. 294, pp. H1133-H1134.
Pantoliano et al., "High Density Miniaturized Thermal Shift Assays as a General Strategy for Drug Discovery*.", Journal of Biomolecular Screening, 2001, vol. 6(6), pp. 429-440.
Pertwee, R.G., "The diverse CB1 and CB2 receptor pharmacology of three plant cannabinoids: D9-tetrahydrocannabinol, cannabidiol and D9-tetrahydrocannabivarin", Brit J Pharmacol, 2008, vol. 153, pp. 199-215.
Piomelli, D., "The Molecular Logic of Endocannabinoid Signalling", Nat Rev Neurosci, 2003, vol. 4, pp. 873-884.
Schlosser et al., "In Search in Simplicity and Flexibility: A Rational Access to Twelve Fluoroindolecarboxylic Acids.", Eur. J. Org. Chem. 2006, pp. 2956.
Sugiura et al., "2-Arachidonoylglycerol: A Possible Endogenous Cannabinoid Receptor Ligand in Brain", Biochem Biophys Res Commun, 1995, vol. 215, pp. 89-97.
Walker et al., "Pain modulation by release of the endogenous cannabinoid anandamide", Proc Natl Acad Sci USA, 1999, vol. 96, pp. 12198-121203.

* cited by examiner

OXOPIPERAZINE-AZETIDINE AMIDES AND OXODIAZEPINE-AZETIDINE AMIDES AS MONOACYLGLYCEROL LIPASE INHIBITORS

CROSS-REFERENCE TO RELATED APPLICATIONS

This application claims the benefit of U.S. Provisional Application No. 61/386,777, filed Sep. 27, 2010.

STATEMENT REGARDING FEDERALLY SPONSORED RESEARCH OR DEVELOPMENT

The research and development of the invention described below was not federally sponsored.

BACKGROUND OF THE INVENTION

*Cannabis sativa* has been used for the treatment of pain for many years. $\Delta^9$-tetrahydrocannabinol is a major active ingredient from *Cannabis sativa* and an agonist of cannabinoid receptors (Pertwee, *Brit J Pharmacol*, 2008, 153, 199-215). Two cannabinoid G protein-coupled receptors have been cloned, cannabinoid receptor type 1 ($CB_1$ Matsuda et al., *Nature*, 1990, 346, 561-4) and cannabinoid receptor type 2 ($CB_2$ Munro et al., *Nature*, 1993, 365, 61-5). $CB_1$ is expressed centrally in brain areas such as, the hypothalamus and nucleus accumbens, as well as peripherally in the liver, gastrointestinal tract, pancreas, adipose tissue, and skeletal muscle (Di Marzo et al., *Curr Opin Lipidol*, 2007, 18, 129-140). $CB_2$ is predominantly expressed in immune cells such as, monocytes (Pacher et al., *Amer J Physiol*, 2008, 294, H1133-H1134), and under certain conditions, also in the brain (Benito et al., *Brit J Pharmacol*, 2008, 153, 277-285) and in skeletal (Cavuoto et al., *Biochem Biophys Res Commun*, 2007, 364, 105-110) and cardiac (Hajrasouliha et al., *Eur J Pharmacol*, 2008, 579, 246-252) muscle. An abundance of pharmacological, anatomical and electrophysiological data, using synthetic agonists, indicate that increased cannabinoid signaling through $CB_1/CB_2$ promotes analgesia in tests of acute nociception and suppresses hyperalgesia in models of chronic neuropathic and inflammatory pain (Cravatt et al., *J Neurobiol*, 2004, 61, 149-60; Guindon et al., *Brit J Pharmacol*, 2008, 153, 319-334).

Efficacy of synthetic cannabinoid receptor agonists is well documented. Moreover, studies using cannabinoid receptor antagonists and knockout mice have also implicated the endocannabinoid system as an important modulator of nociception. Anandamide (AEA) (Devane et al., *Science*, 1992, 258, 1946-9) and 2-arachidinoylglycerol (2-AG) (Mechoulam et al., *Biochem Pharmacol*, 1995, 50, 83-90; Sugiura et al., *Biochem Biophys Res Commun*, 1995, 215, 89-97) are two major endocannabinoids. AEA is hydrolyzed by fatty acid amide hydrolase (FAAH) and 2-AG is hydrolyzed by monoacylglycerol lipase (MGL) (Piomelli, *Nat Rev Neurosci*, 2003, 4, 873-884). Genetic ablation of FAAH elevates endogenous AEA and results in a $CB_1$-dependent analgesia in models of acute and inflammatory pain (Lichtman et al., *Pain*, 2004, 109, 319-27), suggesting that the endocannabinoid system functions naturally to inhibit pain (Cravatt et al., *J Neurobiol*, 2004, 61, 149-60). Unlike the constitutive increase in endocannabinoid levels using FAAH knockout mice, use of specific FAAH inhibitors transiently elevates AEA levels and results in antinociception in vivo (Kathuria et al., *Nat Med*, 2003, 9, 76-81). Further evidence for an endocannabinoid-mediated antinociceptive tone is demonstrated by the formation of AEA in the periaqueductal grey following noxious stimulation in the periphery (Walker et al., *Proc Natl Acad Sci USA*, 1999, 96, 12198-203) and, conversely, by the induction of hyperalgesia following antisense RNA-mediated inhibition of $CB_1$ in the spinal cord (Dogrul et al., *Pain*, 2002, 100, 203-9).

With respect to 2-AG, intravenous delivery of 2-AG produces analgesia in the tail flick (Mechoulam et al., *Biochem Pharmacol*, 1995, 50, 83-90) and hot plate (Lichtman et al., *J Pharmacol Exp Ther*, 2002, 302, 73-9) assays. In contrast, it was demonstrated that 2-AG given alone is not analgesic in the hot plate assay, but when combined with other 2-monoacylglycerols (i.e., 2-linoleoyl glycerol and 2-palmitoyl glycerol), significant analgesia is attained, a phenomenon termed the "entourage effect" (Ben-Shabat et al., *Eur J Pharmacol*, 1998, 353, 23-31). These "entourage" 2-monoacylglycerols are endogenous lipids that are co-released with 2-AG and potentiate endocannabinoid signaling, in part, by inhibiting 2-AG breakdown, most likely by competition for the active site on MGL. This suggests that synthetic MGL Inhibitors will have a similar effect. Indeed, URB602, a relatively weak synthetic MGL Inhibitor, showed an antinociceptive effect in a murine model of acute inflammation (Comelli et al., *Brit J Pharmacol*, 2007, 152, 787-794).

Although the use of synthetic cannabinoid agonists have conclusively demonstrated that increased cannabinoid signaling produces analgesic and anti-inflammatory effects, it has been difficult to separate these beneficial effects from the unwanted side effects of these compounds. An alternative approach is to enhance the signaling of the endocannabinoid system by elevating the level of 2-AG, the endocannabinoid of highest abundance in the central nervous system (CNS) and gastrointestinal tract, which may be achieved by inhibition of MGL. Therefore, MGL inhibitors are potentially useful for the treatment of pain, inflammation, and CNS disorders (Di Marzo et al., *Curr Pharm Des*, 2000, 6, 1361-80; Shaveri et al., *Brit J Pharmacol*, 2007, 152, 624-632; McCarberg Bill et al., *Amer J Ther*, 2007, 14, 475-83), as well as glaucoma and disease states arising from elevated intraocular pressure (Njie, Ya Fatou; He, Fang; Qiao, Zhuanhong; Song, Zhao-Hui, *Exp. Eye Res.*, 2008, 87(2):106-14).

SUMMARY OF THE INVENTION

The present invention is directed to a compound of Formula (Ia)

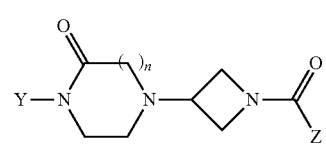

Formula (Ia)

wherein
Y is
  i) a $C_{6-10}$ aryl or
  ii) a heteroaryl selected from the group consisting of thiazolyl, oxazolyl, pyridinyl, and pyrimidinyl,
    wherein Y is unsubstituted or substituted with one or two substituents each of which is independently selected from the group consisting of fluoro, chloro, $C_{1-4}$alkyl, $C_{1-4}$alkoxy, cyano, and trifluoromethyl;
Z is
  i) a $C_{6-10}$ aryl,
  ii) a heteroaryl selected from the group consisting of benzoxazolyl, benzothiazolyl, benzothienyl, indazolyl, and indolyl, or iii) phenylmethyl-phenyl; wherein the phenyl of phenylmethyl is unsubstituted or substituted with one or two substituents each of which is independently selected from the group consisting of bromo, chloro, fluoro, iodo, $C_{1-4}$alkyl, $C_{1-4}$alkoxy, and trifluoromethyl, wherein the $C_{6-10}$ aryl and the heteroaryl of Z are unsubstituted or substituted with one or two substitutents each of which is independently selected from the group consisting of bromo, chloro, fluoro, iodo, $C_{1-4}$alkyl, $C_{1-4}$alkoxy, trifluoromethyl, and phenyl;

provided that no more than one substituent of Z is phenyl and said phenyl is unsubstituted or substituted with one or two substituents each of which is independently selected from the group consisting of trifluoromethyl, chloro, cyano, and fluoro;

n is 1 or 2; and enantiomers, diastereomers, solvates and pharmaceutically acceptable salts thereof.

The present invention is further directed to a compound of Formula (Ib)

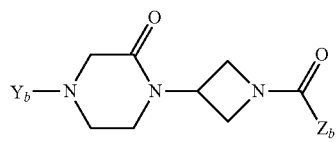

Formula (Ib)

wherein:

$Y_b$ is
  i) a $C_{6-10}$ aryl or
  ii) a heteroaryl selected from the group consisting of thiazolyl, oxazolyl, pyridinyl, and pyrimidinyl,
    wherein $Y_b$ is unsubstituted or substituted with one or two substituents each of which is independently selected from the group consisting of fluoro, chloro, $C_{1-4}$alkyl, $C_{1-4}$alkoxy, cyano, and trifluoromethyl;

$Z_b$ is
  i) a $C_{6-10}$ aryl,
  ii) a heteroaryl selected from the group consisting of benzoxazolyl, benzothiazolyl, benzothienyl, and indolyl, or
  iii) phenylmethyl-phenyl; wherein the phenyl of phenylmethyl is unsubstituted or substituted with one or two substituents each of which is independently selected from the group consisting of bromo, chloro, fluoro, iodo, $C_{1-4}$alkyl, $C_{1-4}$alkoxy, and trifluoromethyl,
    wherein the $C_{6-10}$ aryl and the heteroaryl of $Z_b$ are unsubstituted or substituted with one or two substitutents each of which is independently selected from the group consisting of bromo, chloro, fluoro, iodo, $C_{1-4}$alkyl, $C_{1-4}$alkoxy, trifluoromethyl, and phenyl,
    provided that no more than one substituent of $Z_b$ is phenyl and said phenyl is unsubstituted or substituted with one or two substituents each of which is independently selected from the group consisting of trifluoromethyl, chloro, cyano, and fluoro;

and enantiomers, diastereomers, solvates and pharmaceutically acceptable salts thereof.

The present invention also provides, inter alia, a pharmaceutical composition comprising, consisting of and/or consisting essentially of a pharmaceutically acceptable carrier, a pharmaceutically acceptable excipient, and/or a pharmaceutically acceptable diluent, and a compound of Formula (Ia) or (Ib) or a pharmaceutically acceptable salt form thereof.

Also provided are processes for making a pharmaceutical composition comprising, consisting of, and/or consisting essentially of admixing a compound of Formula (Ia) or (Ib) or a pharmaceutically acceptable salt form thereof, and a pharmaceutically acceptable carrier, a pharmaceutically acceptable excipient, and/or a pharmaceutically acceptable diluent.

The present invention further provides, inter alia, methods for treating or ameliorating a MGL-modulated disorder in a subject, including a human or other mammal in which the disease, syndrome, or condition is affected by the modulation of the MGL enzyme such as pain, and the diseases that lead to such pain, inflammation, and CNS disorders, using a compound of Formula (Ia) or (Ib) or a pharmaceutically acceptable salt form thereof.

The present invention also provides, inter alia, methods for producing the instant compounds and pharmaceutical compositions and medicaments thereof.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, $(C_{1-6}$alkyl$)_2$amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 or more carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "benzo-fused cycloalkyl" refers to a 5- to 8-membered monocyclic cycloalkyl ring fused to a benzene ring. The carbon atom ring members that form the cycloalkyl ring may be fully saturated or partially saturated.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "benzo-fused heterocyclyl" refers to a 5 to 7 membered monocyclic heterocycle ring fused to a benzene ring. The heterocycle ring contains carbon atoms and from 1 to 4 heteroatoms independently selected from N, O, and S. The carbon atom ring members that form the heterocycle ring may be fully saturated or partially saturated. Unless otherwise noted, benzo-fused heterocycle ring is attached to its pendant group at a carbon atom of the benzene ring.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from N, O, and S. Included within the term heteroaryl are aromatic rings of 5 or 6 members wherein the ring consists of carbon atoms and has at least one heteroatom member. Suitable heteroatoms include N, O, and S. In the case of 5 membered rings, the heteroaryl ring preferably contains one member of N, O or S and, in addition, up to 3 additional N atoms. In the case of 6 membered rings, the heteroaryl ring preferably contains from 1 to 3 nitrogen atoms. For the case wherein the 6 membered ring has 3 N, at most 2 nitrogen atoms are adjacent. When a heteroaryl is bicyclic, at least one heteroatom is present in each ring. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl and pyrazinyl. Unless otherwise noted, the heteroaryl is attached to its pendant group at any heteroatom or carbon atom that results in a stable structure.

Unless otherwise noted, the term "benzo fused heteroaryl" refers to a 5 to 6 membered monocyclic heteroaryl ring fused to a benzene ring. The heteroaryl ring contains carbon atoms and from 1 to 4 heteroatoms independently selected from N, O, and S. Examples of heteroaryl groups with the optionally fused benzene rings include indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the benzo-fused heteroaryl is attached to its pendant group at any heteroatom or carbon atom that results in a stable structure.

The term "halogen" or "halo" refers to fluorine, chlorine, bromine and iodine atoms.

The term "formyl" refers to the group —C(=O)H.

The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

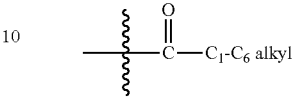

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Compounds with 2 stereocenters both labeled "*RS" and drawn with stereo bond designations are a 2-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of Formula (Ia) and (Ib) can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "MGL inhibitor" is intended to encompass a compound that interacts with MGL to substantially reduce or eliminate its catalytic activity, thereby increasing the concentrations of its substrate(s). The term "MGL-modulated" is used to refer to the condition of being affected by the modulation of the MGL enzyme including the condition of being affected by the inhibition of the MGL enzyme such as pain, and the diseases that lead to such pain, inflammation and CNS disorders.

As used herein, unless otherwise noted, the term "affect" or "affected" (when referring to a disease, syndrome, condition or disorder that is affected by inhibition of MGL) shall include a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of Formula (Ia) and (Ib) are useful in methods for treating, ameliorating and/or preventing a disease, a syndrome, a condition or a disorder that is affected by the inhibition of MGL. Such methods comprise, consist of and/or consist essentially of administering to a subject, including an animal, a mammal, and a human in need of such treatment, amelioration and/or prevention, a therapeutically effective amount of a compound of Formula (Ia) or (Ib), or an enantiomer, diastereomer, solvate or pharmaceutically acceptable salt thereof. In particular, the compounds of Formula (Ia) and (Ib), or an enantiomer, diastereomer, solvate or pharmaceutically acceptable salt thereof are useful for treating, ameliorating and/or preventing pain; diseases, syndromes, conditions, or disorders causing such pain; inflammation and/or CNS disorders. More particularly, the compounds of Formula (Ia) and (Ib), or an enantiomer, diastereomer, solvate or pharmaceutically acceptable salt thereof are useful for treating, ameliorating and/or preventing inflammatory pain, inflammatory hypersensitivity conditions and/or neuropathic pain, comprising administering to a subject in need thereof a therapeutically effective amount of a compound of Formula (Ia) or (Ib), or an enantiomer, diastereomer, solvate or pharmaceutically acceptable salt thereof as herein defined.

Examples of inflammatory pain include pain due to a disease, condition, syndrome, disorder, or a pain state including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache, or arachnoiditis.

One type of inflammatory pain is inflammatory hyperalgesia/hypersensitivity. Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases including Crohn's Disease, ulcerative colitis, urinary incontinence, benign prostatic hypertrophy, cough, asthma, rhinitis, nasal hypersensitivity, itch, contact dermatitis and/or dermal allegy and chronic obstructive pulmonary disease.

In an embodiment, the present invention is directed to a method for treating, ameliorating and/or preventing inflammatory visceral hyperalgesia in which a enhanced visceral irritability exists, comprising, consisting of, and/or consisting essentially of the step of administering to a subject in need of such treatment a therapeutically effective amount of a compound, salt or solvate of Formula (Ia) or (Ib). In a further embodiment, the present invention is directed to a method for treating inflammatory somatic hyperalgesia in which a hypersensitivity to thermal, mechanical and/or chemical stimuli exists, comprising administering to a mammal in need of such treatment a therapeutically effective amount of a compound of Formula (Ia) or (Ib) or an enantiomer, diastereomer, solvate or pharmaceutically acceptable salt thereof.

A further embodiment of the present invention is directed to a method for treating, ameliorating and/or preventing neuropathic pain. Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngeal neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

In a further embodiment, the present invention is directed to a method for treating, ameliorating and/or preventing neuropathic cold allodynia in which a hypersensitivity to a cooling stimuli exists, comprising, consisting of, and/or consisting essentially of the step of administering to a subject in need of such treatment a therapeutically effective amount of a compound of Formula (Ia) or (Ib) or an enantiomer, diastereomer, solvate or pharmaceutically acceptable salt thereof.

In a further embodiment, the present invention is directed to a method for treating, ameliorating and/or preventing CNS disorders. Examples of CNS disorders include anxieties such as, social anxiety, post-traumatic stress disorder, phobias, social phobia, special phobias, panic disorder, obsessive-compulsive disorder, acute stress disorder, separation anxiety disorder, and generalized anxiety disorder, as well as depression such as, major depression, bipolar disorder, seasonal affective disorder, post natal depression, manic depression, and bipolar depression.

Embodiments of the present invention include a compound of Formula (Ia)

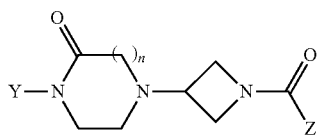

Formula (Ia)

wherein:
a) Y is
   i) phenyl or
   ii) a heteroaryl that is thiazolyl or pyrimidinyl;
b) Y is thiazolyl or pyrimidinyl;
c) Z is
   i) a $C_{6-10}$ aryl or
   ii) a heteroaryl selected from the group consisting of benzoxazolyl, benzothiazolyl, benzothienyl, and indolyl,
      wherein $C_{6-10}$ aryl and heteroaryl of Z are optionally independently substituted with one to two substitutents selected from the group consisting of chloro, fluoro, $C_{1-4}$alkyl, trifluoromethyl, and phenyl,
   provided that no more than one substituent of is phenyl and said phenyl is unsubstituted or substituted with one or two substituents each of which is trifluoromethyl or fluoro;
d) Z is a heteroaryl selected from the group consisting of benzoxazolyl, benzothiazolyl, benzothienyl, and indolyl,
   wherein the heteroaryl of Z is unsubstituted or substituted with one or two substitutents each of which is independently selected from the group consisting of chloro, trifluoromethyl, and phenyl,
   provided that no more than one substituent of Z is phenyl and said phenyl is unsubstituted or substituted with one or two substituents each of which is trifluoromethyl or fluoro;
   n is 1; n is 2;

and any combination of embodiments a) through f) above, provided that it is understood that combinations in which different embodiments of the same substituent would be combined are excluded;
and enantiomers, diastereomers, solvates, and pharmaceutically acceptable salts thereof.

An embodiment of the present invention includes a compound of Formula (Ia)

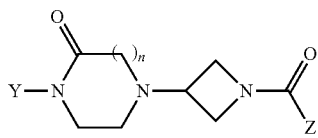

Formula (Ia)

wherein:
Y is
   i) phenyl, or
   ii) a heteroaryl that is thiazolyl or pyrimidinyl;
Z is
   i) $C_{6-10}$ aryl, or
   ii) a heteroaryl selected from the group consisting of benzoxazolyl, benzothiazolyl, benzothienyl, and indolyl,
   wherein the $C_{6-10}$ aryl and the heteroaryl of Z are unsubstituted or substituted with one or two substitutents each of which is selected from the group consisting of chloro, fluoro, $C_{1-4}$alkyl, trifluoromethyl, and phenyl;
   provided that no more than one substituent of Z is phenyl and said phenyl is unsubstituted or substituted with one or two substituents each of which is trifluoromethyl or fluoro;
n is 1 or 2; and enantiomers, diastereomers, solvates and pharmaceutically acceptable salts thereof.

A further embodiment of the present invention includes a compound of Formula (Ia)

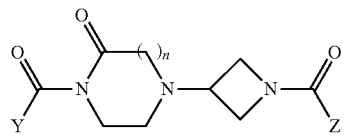

Formula (Ia)

wherein:
Y is
   i) phenyl or
   ii) a heteroaryl that is thiazolyl or pyrimidinyl;
Z is
   i) a $C_{6-10}$ aryl or
   ii) a heteroaryl selected from the group consisting of benzoxazolyl, benzothiazolyl, benzothienyl, and indolyl,
      wherein the $C_{6-10}$ aryl and the heteroaryl of Z are unsubstituted or substituted with one or two substitutents each of which is independently selected from the group consisting of chloro, fluoro, $C_{1-4}$alkyl, trifluoromethyl, and phenyl,
      provided that no more than one substituent of Z is phenyl and said phenyl is unsubstituted or substituted with one or two substituents each of which is trifluoromethyl or fluoro;
n is 1; and enantiomers, diastereomers, solvates, and pharmaceutically acceptable salts thereof.

An embodiment of the present invention includes a compound of Formula (Ia)

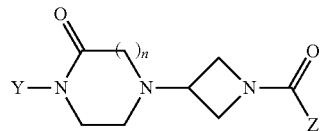

Formula (Ia)

wherein:
Y is thiazolyl or pyrimidinyl;
Z is a heteroaryl selected from the group consisting of benzoxazolyl, benzothiazolyl, benzothienyl, and indolyl,
   wherein the heteroaryl of Z is unsubstituted or substituted with one or two substitutents each of which is independently selected from the group consisting of chloro, trifluoromethyl, and phenyl,
   provided that no more than one substituent of Z is phenyl and said phenyl is unsubstituted or substituted with one or two substituents each of which is trifluoromethyl or fluoro;
n is 1 or 2;
and enantiomers, diastereomers, solvates, and pharmaceutically acceptable salts thereof.

An embodiment of the present invention includes a compound of Formula (Ia)

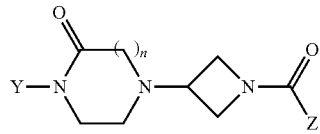

Formula (Ia)

wherein:
Y is thiazolyl or pyrimidinyl;
Z is a heteroaryl selected from the group consisting of benzoxazolyl, benzothiazolyl, benzothienyl, and indolyl,
wherein the heteroaryl of Z is unsubstituted or substituted with one or two substitutents each of which is independently selected from the group consisting of chloro, trifluoromethyl, and phenyl,
provided that no more than one substituent of Z is phenyl and said phenyl is unsubstituted or substituted with one or two substituents each of which is trifluoromethyl or fluoro;
n is 1;
and enantiomers, diastereomers, solvates, and pharmaceutically acceptable salts thereof.

A further embodiment of the present invention includes a compound of Formula (Ia)

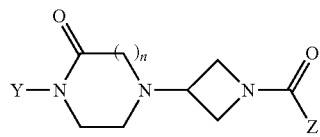

Formula (Ia)

wherein:
Y is
  i) phenyl or
  ii) a heteroaryl that is thiazolyl or pyrimidinyl;
Z is
  i) a $C_{6-10}$ aryl or
  ii) a heteroaryl selected from the group consisting of benzoxazolyl, benzothiazolyl, benzothienyl, and indolyl,
    wherein the $C_{6-10}$ aryl and the heteroaryl of Z are unsubstituted or substituted with one or two substitutents each of which is independently selected from the group consisting of chloro, fluoro, $C_{1-4}$alkyl, trifluoromethyl, and phenyl,
    provided that no more than one substituent of Z is phenyl and said phenyl is unsubstituted or substituted with one or two substituents each of which is trifluoromethyl or fluoro;
n is 2; and enantiomers, diastereomers, solvates, and pharmaceutically acceptable salts thereof.

The present invention is further directed to a compound of Formula (Ia)

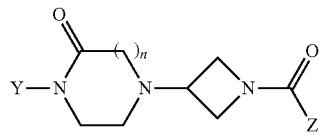

Formula (Ia)

selected from the group consisting of
the compound wherein Y is phenyl, Z is 4-(phenylmethyl)-phenyl, and n is 1;
the compound wherein Y is phenyl, Z is 4-phenyl-phenyl, and n is 1;
the compound wherein Y is pyrimidin-2-yl, Z is 1-(4-trifluoromethyl-phenyl)-1H-indol-5-yl, and n is 1;
the compound wherein Y is pyrimidin-2-yl, Z is 1-(4-fluoro-phenyl)-1H-indol-5-yl, and n is 1;
the compound wherein Y is thiazol-2-yl, Z is 1-(4-fluoro-phenyl)-1H-indol-5-yl, and n is 1;
the compound wherein Y is thiazol-4-yl, Z is 1-(4-fluoro-phenyl)-1H-indol-5-yl, and n is 1;
the compound wherein Y is thiazol-4-yl, Z is 3-chloro-6-trifluoromethyl-benzothien-2-yl, and n is 1;
the compound wherein Y is pyrimidin-2-yl, Z is 3-chloro-6-trifluoromethyl-benzothien-2-yl, and n is 1;
the compound wherein Y is pyrimidin-2-yl, Z is 4-phenyl-phenyl, and n is 1;
the compound wherein Y is pyrimidin-2-yl, Z is 2-phenyl-benzothiazol-6-yl, and n is 1;
the compound wherein Y is thiazol-2-yl, Z is 3-chloro-6-trifluoromethyl-benzothien-2-yl, and n is 1;
the compound wherein Y is thiazol-2-yl, Z is 2-phenyl-benzothiazol-6-yl, and n is 1;
the compound wherein Y is phenyl, Z is 1-(4-trifluoromethyl-phenyl)-1H-indol-5-yl, and n is 1;
the compound wherein Y is phenyl, Z is 3-chloro-6-trifluoromethyl-benzothien-2-yl, and n is 1;
the compound wherein Y is phenyl, Z is 1-(3,4-difluoro-phenyl)-1H-indol-5-yl, and n is 1;
the compound wherein Y is thiazol-2-yl, Z is 2-phenyl-benzoxazol-6-yl, and n is 1;
the compound wherein Y is pyrimidin-2-yl, Z is 3-chloro-6-trifluoromethyl-benzothien-2-yl, and n is 2;
the compound wherein Y is thiazol-2-yl, Z is 4-phenyl-phenyl, and n is 1;
the compound wherein Y is thiazol-2-yl, Z is 3-chloro-6-trifluoromethyl-benzothien-2-yl, and n is 2;
the compound wherein Y is pyrimidin-2-yl, Z is 1-(4-fluoro-phenyl)-1H-indol-5-yl, and n is 2;
the compound wherein Y is thiazol-2-yl, Z is 1-(4-fluoro-phenyl)-1H-indol-5-yl, and n is 2;
the compound wherein Y is thiazol-2-yl, Z is 2-phenyl-benzoxazol-6-yl, and n is 2;
and pharmaceutically acceptable salt forms thereof.

Embodiments of the present invention are directed to a compound of Formula (Ib)

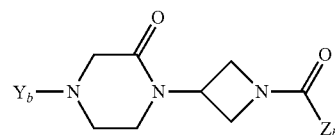

Formula (Ib)

wherein:
a) $Y_b$ is thiazolyl or pyrimidinyl;
b) $Z_b$ is a heteroaryl selected from the group consisting of benzoxazolyl, benzothiazolyl, benzothienyl, and indolyl, wherein the heteroaryl of $Z_b$ is unsubstituted or substituted with one or two substitutents each of which is independently selected from the group consisting of bromo, chloro, fluoro, trifluoromethyl, and phenyl, provided that no more than one substituent of $Z_b$ is phenyl and said phenyl is unsubstituted or substituted with one or two substitutents each of which is trifluoromethyl or fluoro;

c) $Z_b$ is benzothienyl or indolyl, wherein $Z_b$ is unsubstituted or substituted with one or two substitutents each of which is trifluoromethyl or phenyl, provided that no more than one substituent of $Z_b$ is phenyl and said phenyl substituent is unsubstituted or substituted with one trifluoromethyl or fluoro substituent;

and any combination of embodiments a) through c) above, provided that it is understood that combinations in which different embodiments of the same substituent would be combined are excluded;

and enantiomers, diastereomers, solvates, and pharmaceutically acceptable salts thereof.

An embodiment of the present invention is directed to a compound of Formula (Ib)

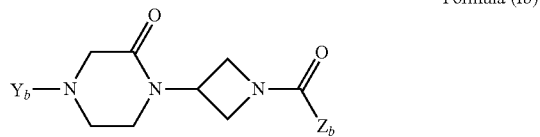

Formula (Ib)

wherein:

$Y_b$ is thiazolyl or pyrimidinyl;

$Z_b$ is a heteroaryl selected from the group consisting of benzoxazolyl, benzothiazolyl, benzothienyl, and indolyl, wherein the heteroaryl of $Z_b$ is unsubstituted or substituted with one or two substitutents each of which is independently selected from the group consisting of bromo, chloro, fluoro, trifluoromethyl, and phenyl, provided that no more than one substituent of $Z_b$ is phenyl and said phenyl is unsubstituted or substituted with one or two substituents each of which is trifluoromethyl or fluoro;

and enantiomers, diastereomers, solvates, and pharmaceutically acceptable salts thereof.

An embodiment of the present invention is directed to a compound of Formula (Ib)

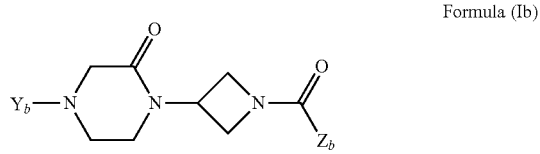

Formula (Ib)

wherein:

$Y_b$ is thiazolyl or pyrimidinyl;

$Z_b$ is a heteroaryl selected from the group consisting of benzothienyl and indolyl;

wherein the heteroaryl of $Z_b$ is unsubstituted or substituted with one or two substitutents each of which is trifluoromethyl or phenyl, provided that no more than one substituent of $Z_b$ is phenyl and said phenyl is unsubstituted or substituted with one trifluoromethyl or fluoro substitutent;

and enantiomers, diastereomers, solvates, and pharmaceutically acceptable salts thereof.

An embodiment of the present invention is directed to a compound of Formula (Ib)

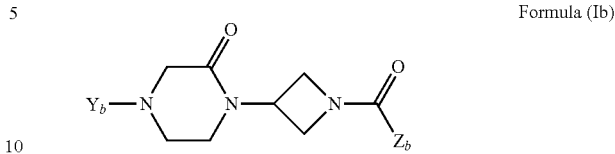

Formula (Ib)

that is the compound wherein $Y_b$ is pyrimidin-2-yl, and $Z_b$ is 6-trifluoromethyl-benzothien-2-yl; or the compound wherein $Y_b$ is pyrimidin-2-yl, and $Z_b$ is 1-(4-trifluoromethyl-phenyl)-1H-indol-5-yl;

or a pharmaceutically acceptable salt thereof.

For use in medicine, salts of compounds of Formula (Ia) and (Ib) refer to non-toxic "pharmaceutically acceptable salts." Other salts may, however, be useful in the preparation of compounds of Formula (Ia) and (Ib) or of their pharmaceutically acceptable salts thereof. Suitable pharmaceutically acceptable salts of compounds of Formula (Ia) and (Ib) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (Ia) and (Ib) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2- naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholin, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (Ia) and (Ib). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (Ia) and (Ib).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (Ia) or (Ib) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as.

$$\%(+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (Ia) or (Ib) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (Ia) or (Ib) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (Ia) and (Ib) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (Ia) and (Ib) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (Ia) or (Ib) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (Ia) or (Ib) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (Ia) or (Ib) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (Ia) or (Ib).

Advantageously, a compound of Formula (Ia) or (Ib) may be administered in a single daily dose, or the total daily dosage may be administered in divided doses of two, three and four times daily.

Optimal dosages of a compound of Formula (Ia) or (Ib) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (Ia) or (Ib) may be administered in any of the foregoing compositions and dosage regimens or by means of those compositions and dosage regimens established in the art whenever use of a compound of Formula (Ia) or (Ib) is required for a subject in need thereof.

As MGL Inhibitors, the compounds of Formula (Ia) and (Ib) are useful in methods for treating and preventing a disease, a syndrome, a condition or a disorder in a subject, including an animal, a mammal and a human in which the disease, the syndrome, the condition or the disorder is affected by the modulation, including inhibition, of the MGL enzyme. Such methods comprise, consist of and/or consist essentially of administering to a subject, including an animal, a mammal, and a human in need of such treatment or prevention a therapeutically effective amount of a compound, salt or solvate of Formula (Ia) or (Ib).

GENERAL SYNTHETIC METHODS

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:

AcCl acetyl chloride
AcOH glacial acetic acid
aq. aqueous
Bn or Bzl benzyl
Boc tert-butyloxycarbonyl
conc. Concentrated
DCC N,N'-dicyclohexyl-carbodiimide
DCE 1,2-dichloroethane
DCM dichloromethane
DIPEA diisopropyl-ethyl amine
DMAP 4-dimethylaminopyridine
DMF N,N-dimethylformamide DMSO dimethylsulfoxide
DPPA diphenylphosphoryl azide
EDC N-(3-dimethylaminopropyl)-N'-ethylcarbodiimide hydrochloride
ESI electrospray ionization
EtOAc ethyl acetate
EtOH ethanol
h hour(s)
HATU O-(1H-7-azabenzotriazol-1-yl)-1,1,3,3-tetramethyluronium hexafluorophosphate
HBTU O-(1H-benzotriazol-1-yl)-1,1,3,3-tetramethyluronium hexafluorophosphate
HEK human embryonic kidney
HEPES (4-(2-hydroxyethyl)-1-piperazineethane sulfonic acid
HPLC high performance liquid chromatography
mCPBA meta-chloroperoxybenzoic acid
MeCN acetonitrile
MeOH methanol
MeOTf methyl triflate
MHz megahertz
min minutes
MS mass spectrometry
NMR nuclear magnetic resonance
PIPES Piperazine-N,N'-bis(2-ethanesulfonic acid)
PyBrOP bromo-tris-pyrrolidinophosphonium hexafluorophosphate
RP reverse-phase
$R_t$ retention time
TEA or $Et_3N$ triethylamine
TFA trifluoroacetic acid
THF tetrahydrofuran
TLC thin layer chromatography
TMS tetramethylsilane Scheme A illustrates a route for the synthesis of compounds of Formula (Ia), wherein Y and Z are as defined herein.

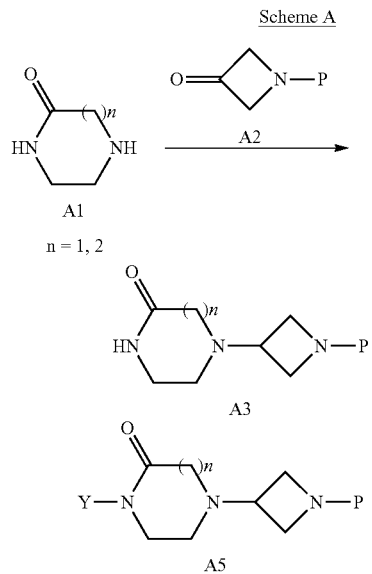

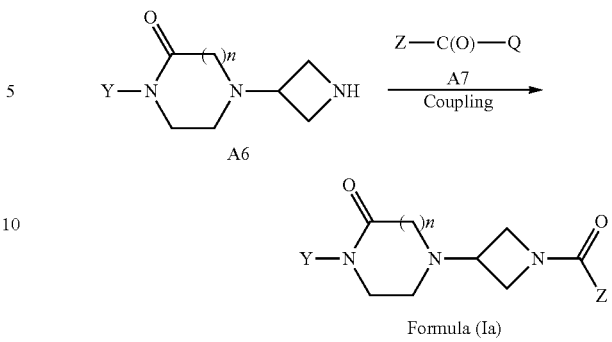

Formula (Ia)

A compound of formula A1 is either commercially available or may be prepared by known methods described in the scientific literature. A compound of formula A1 may undergo a reductive amination with a compound of formula A2 (wherein P is a conventional amino protecting group such as, Boc, Fmoc, Cbz, and the like) in the presence of a hydride source such as, sodium triacetoxyborohydride to afford a compound of formula A3. The Y group of the present invention may be introduced by reaction with a compound of formula A4, Y—X, (wherein X is a suitable leaving group such as, bromo or iodo, and, under certain reaction conditions, may be chloro or triflate) in the presence of copper iodide, 1,10-phenanthroline, and potassium phosphate, to afford a compound of formula A5. Removal of the protecting group (P) by conventional methods affords a compound of formula A6. A compound of formula A6 may be treated with a carboxylic acid of formula A7 wherein Q is hydroxy, in the presence of an appropriate coupling agent such as, HATU, DCC, EDC, HBTU, PyBrOP, and the like; and optionally in the presence of a base such as, DIPEA, to afford a compound of Formula (Ia). Similarly, an acid chloride of formula A7 wherein Q is chloro may be used to effect the acylation of a compound of formula A6. In such case a non-nucleophilic base such as, pyridine, may be added to afford a compound of Formula (Ia).

Scheme B illustrates a route for the synthesis of compounds of Formula (Ib), wherein $Y_b$ and $Z_b$ are as defined herein.

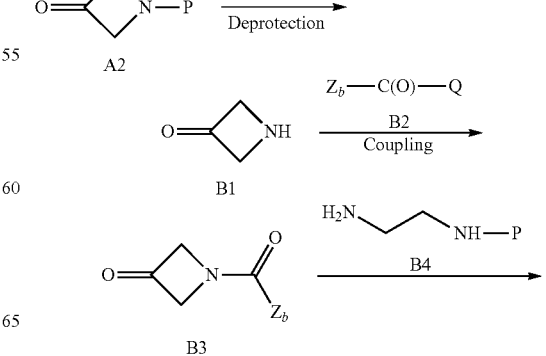

-continued

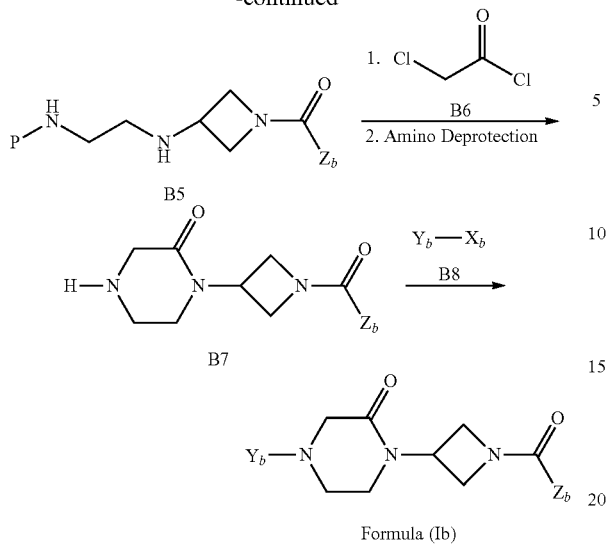

Formula (Ib)

A compound of formula A2 is commercially available and may be deprotected using conventional chemistry to afford the corresponding amine of formula B1. Treatment of a compound of formula B1 with a compound of formula B2, in an analogous manner to the procedure described in scheme A for compound A7, affords a compound of formula B3. Reductive amination with a diamine of formula B4 (wherein P is a conventional amino protecting group) in the presence of a hydride source such as, sodium triacetoxyborohydride, affords a compound of formula B5. Acylation with an acid chloride of formula B6 followed by conventional removal of protecting group (P) provides the cyclized product of formula B7. A compound of formula B7 may be treated with a compound of formula B8 (wherein $X_b$ is fluoro, bromo, chloro, iodo, or triflate) under suitable reaction conditions to afford a compound of Formula (Ib). For example, when $Y_b$ is 2-pyrimidinyl, 4-pyrimidinyl, 2-pyridinyl, 2-thiazolyl, or 2-oxazolyl, the addition of a compound of formula B8 in the presence of a base such as, potassium carbonate or sodium bicarbonate, will provide the desired compounds of Formula (Ib). Alternatively, other $Y_b$ groups of the present invention may be incorporated by the addition of $Y_b$—$X_b$ (B8) in the presence of a palladium catalyst, optionally with a phosphine ligand, and in the presence of an inorganic base such as, potassium carbonate.

Scheme C illustrates an alternate route for the synthesis of compounds of Formula (Ib), wherein $Y_b$ and $Z_b$ are as defined herein.

Scheme C

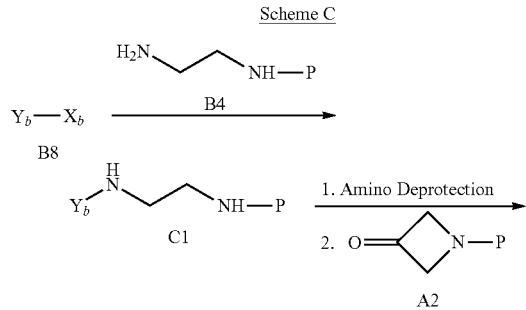

-continued

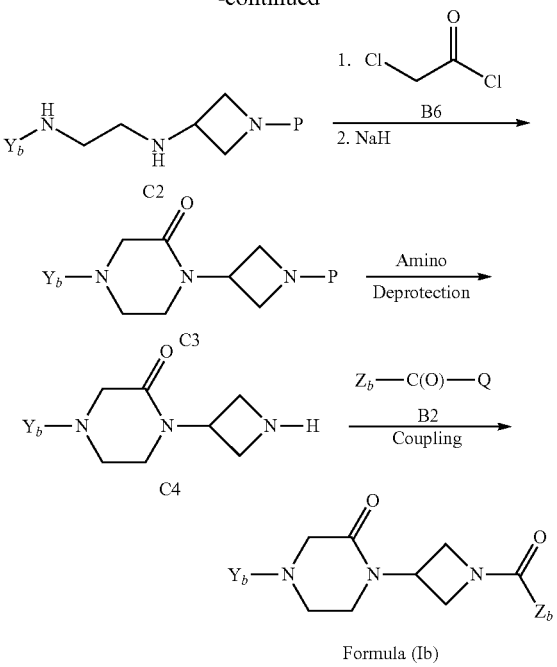

Formula (Ib)

A compound of formula B8 (either commercially available or prepared by known methods found in the scientific literature) may be treated with a compound of formula B4 to afford a compound of formula C1. More specifically, when $Y_b$ of formula B8 is 2-pyrimidinyl, 4-pyrimidinyl, 2-pyridinyl, 2-thiazolyl, or 2-oxazolyl, the addition of a compound of formula B8 in the presence of a base such as, potassium carbonate or sodium bicarbonate, will provide the desired compounds of formula C1. Alternatively, other $Y_b$ groups of the present invention may be incorporated by the addition of B8 in the presence of a palladium catalyst, optionally with a phosphine ligand, and in the presence of an inorganic base such as, potassium carbonate. Conventional removal of the amino protecting group (P) followed by reductive alkylation with a compound of formula A2 affords a compound of formula C2. Acylation with a compound of formula B6 followed by treatment with a strong base such as, sodium hydride, affords the cyclized product of formula C3. Amino deprotection gives the corresponding free amine of formula C4, which, upon acylation with a compound of formula B2 as previously described, affords compounds of Formula (Ib).

Scheme D illustrates the preparation of certain useful intermediates of formulae A7 and B2 (Q is hydroxy) wherein $Z/Z_b$ is a heteroaryl substituted with an optionally substituted phenyl group ($Ar_D$). For illustrative purposes only, the heteroaryl ring is represented by an indole.

Scheme D

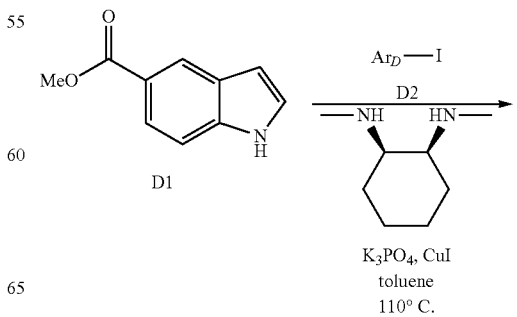

-continued

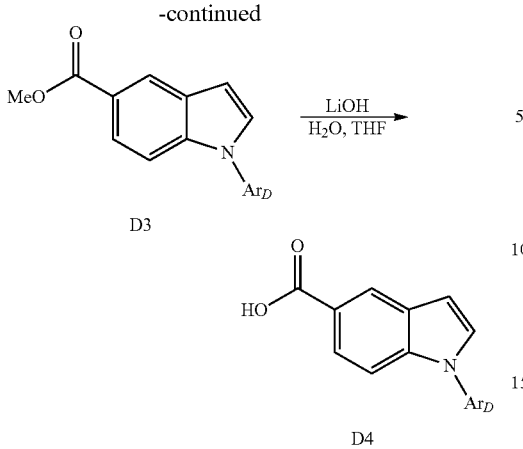

A compound of formula D1 is either commercially available or may be prepared by known methods described in the scientific literature. The compound D1 may be treated with an phenyl iodide of formula D2 in the presence of copper iodide, trans-N,N'-dimethylcyclohexane-1,2-diamine, and potassium phosphate to afford a compound of formula D3. Subsequent saponification affords useful carboxylic acid intermediates of formula D4.

Scheme E illustrates the preparation of certain useful intermediates of formula A7 and B2 (Q is hydroxy) wherein Z/$Z_b$ is benzoxazolyl substituted with an optionally substituted phenyl group (Ar$_E$).

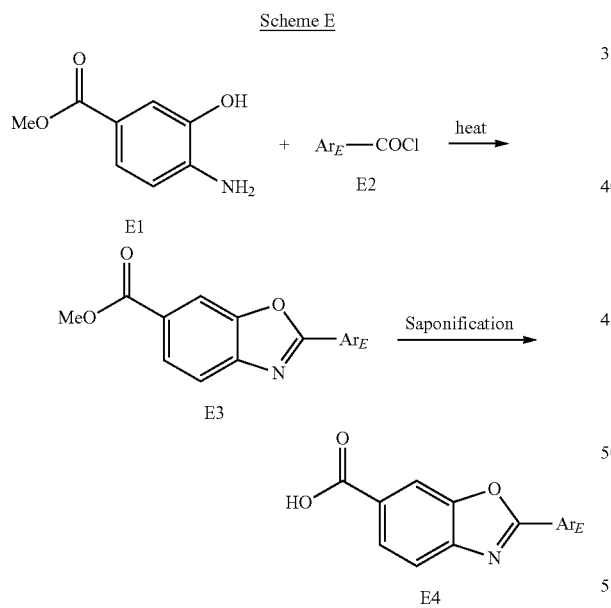

A compound of formula E1 is either commercially available or may be prepared by known methods described in the scientific literature. The compound of formula E1 may be treated with an optionally substituted benzoyl chloride of formula E2 in an organic solvent such as, dioxane, at an elevated temperature to afford the substituted benzoxazole of formula E3. Subsequent saponification affords useful carboxylic acid intermediates of formula E4.

Scheme F illustrates the preparation of certain useful intermediates of formulae A7 and B2 (Q is hydroxy) wherein Z/$Z_b$ is an optionally substituted benzothienyl group, and R$_F$ represents appropriate substituents as defined in Formula (Ia) and Formula (Ib).

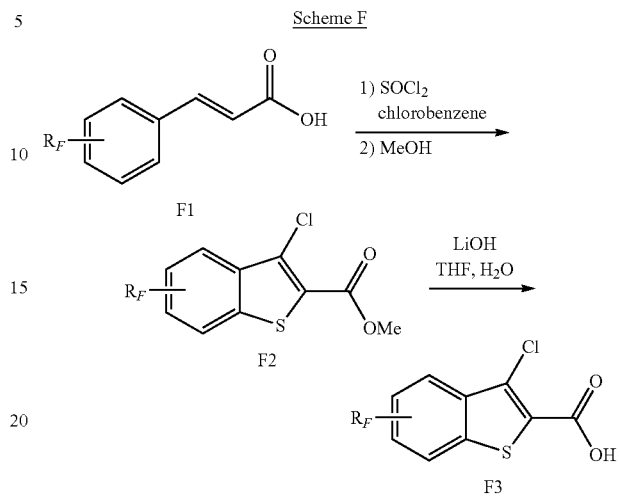

A compound of formula F1 is either commercially available or may be prepared by known methods described in the scientific literature. The compound of formula F1 may be treated with thionyl chloride in an aprotic organic solvent, followed by treatment with methanol to afford a compound of formula F2. Subsequent saponification affords useful carboxylic acid intermediates of formula F3. One skilled in the art will recognize that asymmetrically substituted compounds of formula F1 could lead to mixtures of positional isomers upon cyclization with thionyl chloride. The isomers may then be separated and isolated using conventional chromatography known to those skilled in the art.

Scheme G illustrates the preparation of certain useful intermediates of formulae A7 and B2 (Q is hydroxy) wherein Z/$Z_b$ is phenyl substituted by an optionally substituted phenylmethyl (Ar$_T$-methyl) group.

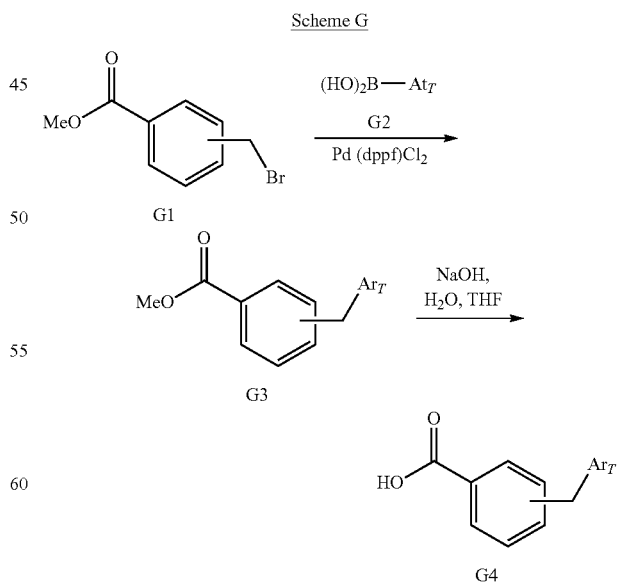

A compound of formula G1 is either commercially available or may be prepared by known methods described in the scientific literature. The compound of formula G1 may be treated with with an appropriately substituted boronic acid or ester of formula G2, in the presence of a palladium catalyst and a suitable base such as, potassium carbonate to afford a compound of formula G3. Subsequent saponification affords useful carboxylic acid intermediates of formula G4.

Scheme H illustrates the preparation of certain useful intermediates of formulae A7 and B2 (Q is hydroxy) wherein $Z/Z_b$ is a benzothienyl group substituted with a fluoro substituent and an optionally substituted phenyl group ($Ar_H$).

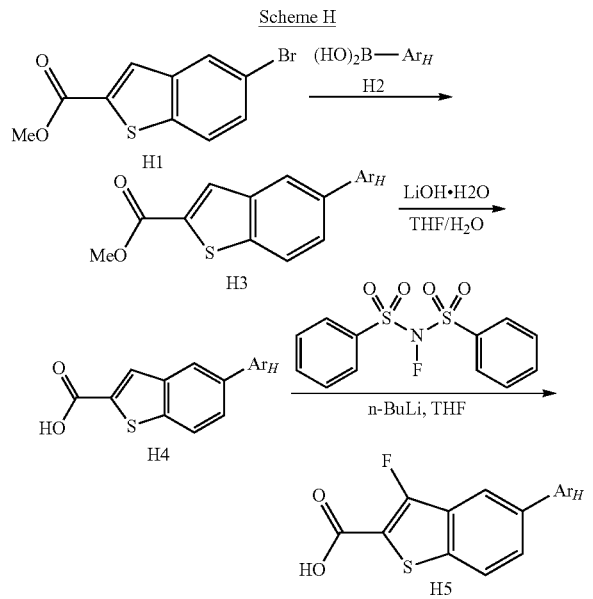

A compound of formula H1 is either commercially available or may be prepared by known methods described in the scientific literature. The compound of formula H1 may be cross-coupled with a boronic acid or ester (H2) in the presence of a palladium catalyst; and in the presence of a suitable base such as, potassium carbonate, to afford a compound of formula H3. Saponification affords the corresponding carboxylic acid H4, which may be treated with N-fluorobenzenesulfonimide in the presence of an organometallic base such as, n-butyl-lithium, to afford the fluorinated compound of formula H5.

Scheme I illustrates the preparation of certain useful intermediates of formulae A7 and B2 (Q is hydroxy) wherein $Z/Z_b$ is a benzothiazole group substituted with an optionally substituted phenyl group ($Ar_I$).

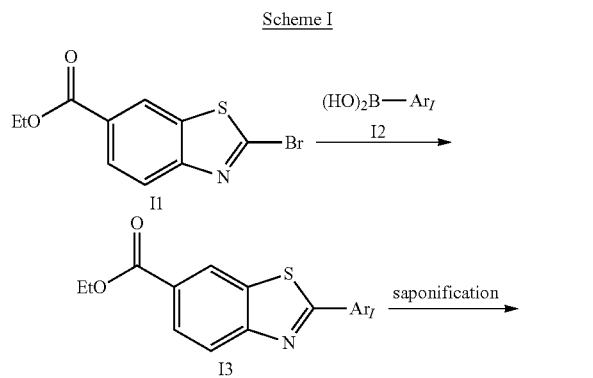

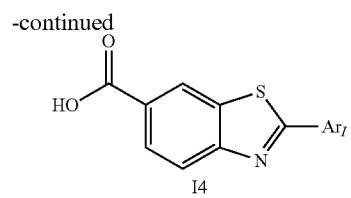

A compound of formula I1 is either commercially available or may be prepared by known methods described in the scientific literature. The compound of formula I1 may be cross-coupled with a boronic acid or ester (I2) in the presence of a palladium catalyst; and in the presence of a suitable base such as, potassium carbonate, to afford a compound of formula I3. Saponification affords the corresponding carboxylic acid of formula I4.

EXAMPLE 1

4-Pyrimidin-2-yl-1-(1-{[6-(trifluoromethyl)-1-benzothiophen-2-yl]carbonyl}azetidin-3-yl)piperazin-2-one, Cpd 23

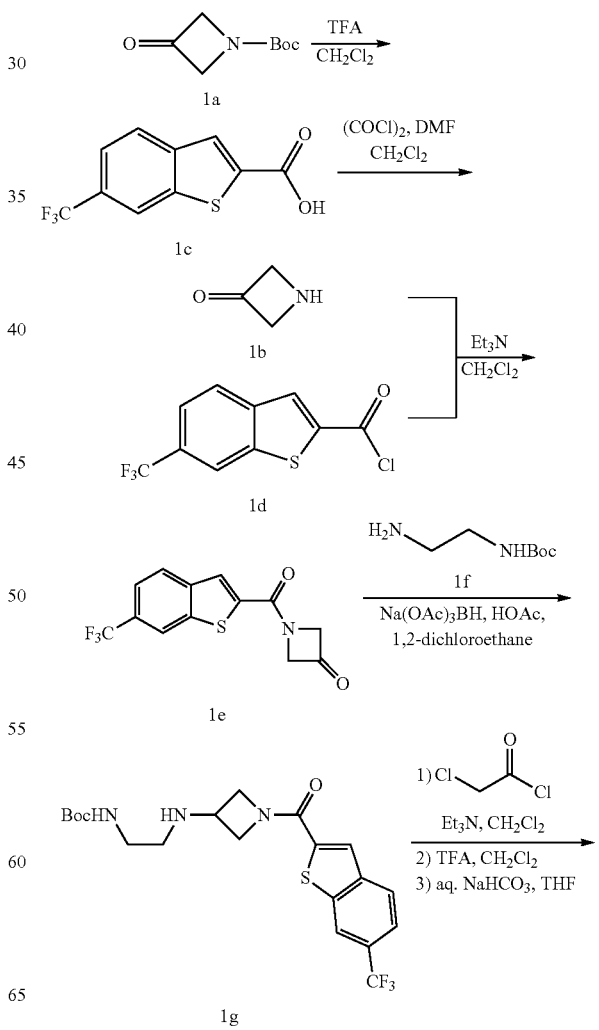

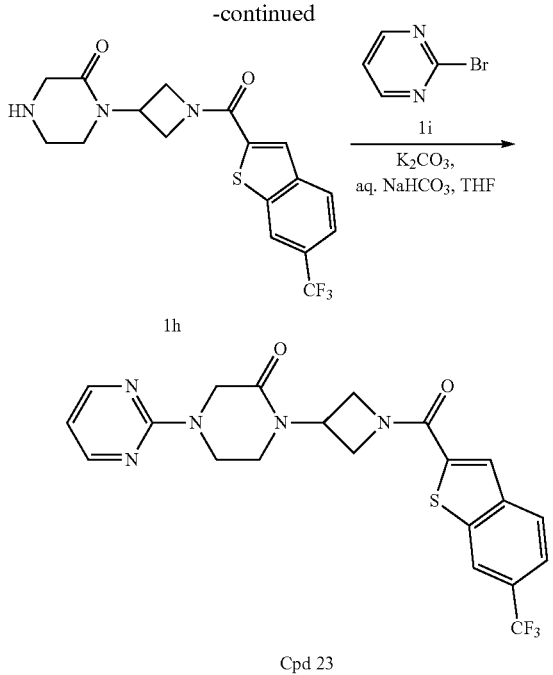

Step A. 1-(6-Trifluoromethyl-benzo[b]thiophene-2-carbonyl)-azetidin-3-one 1e. A solution of N-Boc-azetidin-3-one 1a (171 mg, 1.0 mmol) and TFA (1 mL) in CH$_2$Cl$_2$ (4 mL) was stirred at room temperature for 2 h. The solution was concentrated to give intermediate 1b, which was used in next step without further purification. To a suspension of 6-trifluoromethyl-benzo[b]thiophene-2-carboxylic acid 1c (246 mg, 1.0 mmol) in CH$_2$Cl$_2$ (10 mL) was added oxalyl chloride (0.105 mL, 1.2 mmol), followed by DMF (2 drops). The reaction mixture was stirred at room temperature for 4 h, and concentrated to give the acid chloride 1d, which was used in next step without further purification. To a solution of 1b (1.0 mmol) and Et$_3$N (0.835 mL, 6.0 mmol) in CH$_2$Cl$_2$ (7 mL) at 0° C. was added a solution of 1d (1.0 mmol) in CH$_2$Cl$_2$ (5 mL). The reaction mixture was slowly warmed to room temperature in 2 h, and was quenched with aq. NaHCO$_3$. The resulting mixture was extracted with CH$_2$Cl$_2$. The organic solution was dried over Na$_2$SO$_4$ and concentrated. Purification by column chromatography (silica gel, 40% EtOAc/heptane) gave intermediate 1e as white solid (100 mg).

Step B. {2-[1-(6-Trifluoromethyl-benzo[b]thiophene-2-carbonyl)-azetidin-3-ylamino]-ethyl}-carbamic acid tert-butyl ester 1g.

To a mixture of 1e (62 mg, 0.207 mmol), N-Boc-ethylenediamine 1f (100 mg, 0.62 mmol), and acetic acid (0.3 mL) in 1,2-dichloroethane (3 mL) was added Na(OAc)$_3$BH (53 mg, 0.25 mmol). The reaction mixture was stirred at room temperature overnight, and was then quenched with aq. NaHCO$_3$. The resulting mixture was extracted with CH$_2$Cl$_2$. The organic solution was dried over Na$_2$SO$_4$ and concentrated. Purification by column chromatography (silica gel, 4% MeOH/CH$_2$Cl$_2$) gave intermediate 1g as colorless oil (30 mg).

Step C. Cpd 23

To a solution of 1g (30 mg, 0.068 mmol) and Et$_3$N (0.04 mL, 0.28 mmol) in CH$_2$Cl$_2$ (3 mL) at 0° C. was added chloroacetyl chloride (11.5 mg, 0.10 mmol). The reaction was stirred at 0° C. for 1.5 h, and was then quenched with aq. NaHCO$_3$. The resulting mixture was extracted with CH$_2$Cl$_2$. The organic solution was dried over Na$_2$SO$_4$ and concentrated. The resulting residue was stirred with TFA (0.5 mL) in CH$_2$Cl$_2$ (2 mL) for 1.5 h. The solution was concentrated, and the residue was stirred in aq. NaHCO$_3$ (2 mL) and THF (3 mL) for 24 h. To the resulting intermediate 1h in this mixture of aq. NaHCO$_3$ and THF was added K$_2$CO$_3$ (28 mg, 0.20 mmol) and 2-bromopyrimidine (32 mg, 0.20 mmol). The reaction mixture was heated to reflux for 16 h, and was then extracted with CH$_2$Cl$_2$. The organic solution was dried over Na$_2$SO$_4$ and concentrated. Purification by column chromatography (silica gel, 3% MeOH/CH$_2$Cl$_2$) gave Cpd 23 as a white solid (7 mg). MS 462 (M+H$^+$).

EXAMPLE 2

4-Pyrimidin-2-yl-1-[1-({1-[4-(trifluoromethyl)phenyl]-1H-indol-5-yl}carbonyl)azetidin-3-yl]piperazin-2-one, Cpd 24

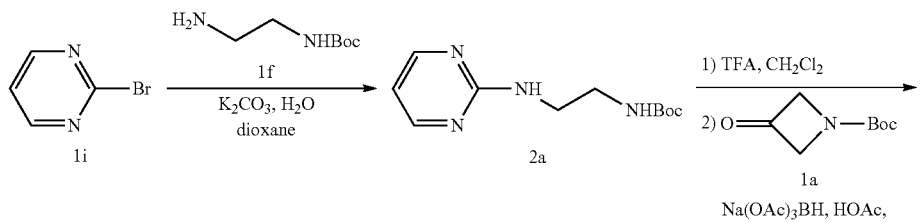

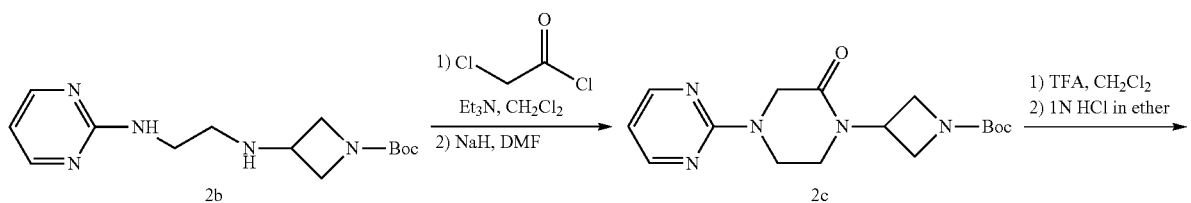

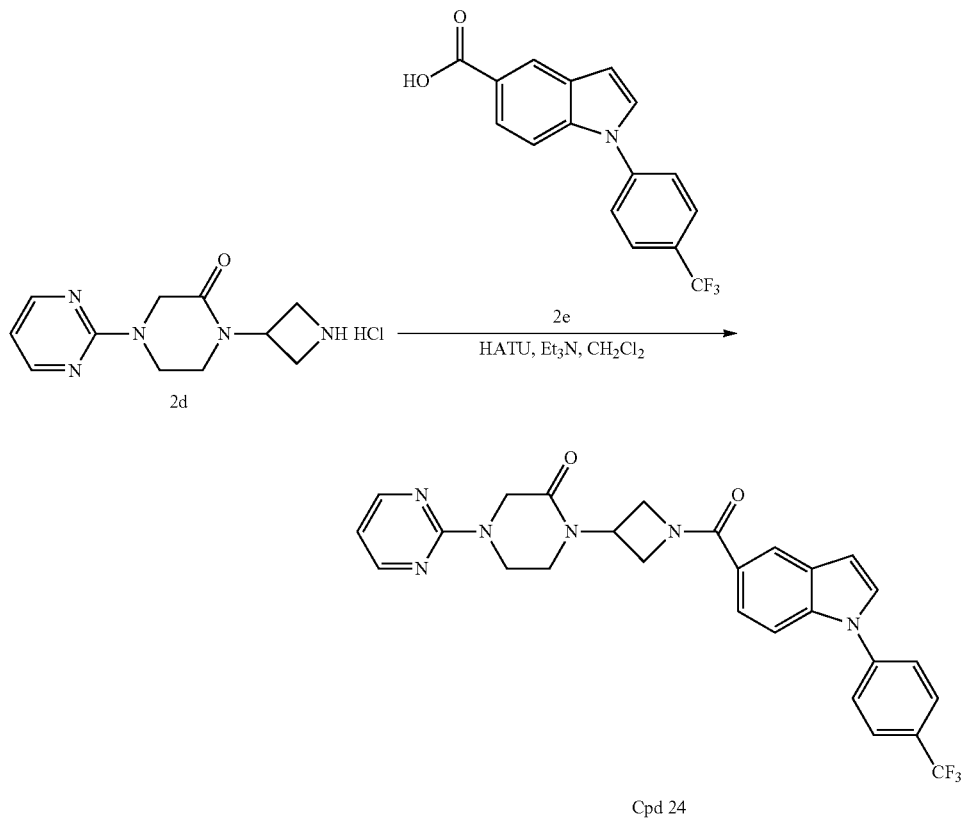

Step A. [2-(Pyrimidin-2-ylamino)-ethyl]-carbamic acid tert-butyl ester 2a. A mixture of 2-bromopyrimidine 1i (600 mg, 3.77 mmol), N-Boc-ethylenediamine 1f (1000 mg, 6.24 mmol), and K₂CO₃ (781 mg, 5.66 mmol) in dioxane (20 mL) and H₂O (10 mL) was heated to reflux for 9 h. The mixture was concentrated to remove most of dioxane, and the resulting mixture was extracted with EtOAc. The organic solution was washed with aq. NaCl, dried over Na₂SO₄ and concentrated. Purification by column chromatography (silica gel, 50% EtOAc/heptane) gave intermediate 2a as white solid (770 mg).

Step B. 3-[2-(Pyrimidin-2-ylamino)-ethylamino]-azetidine-1-carboxylic acid tert-butyl ester 2b.

A solution of intermediate 2a (610 mg, 2.56 mmol) in TFA (2 mL) and CH₂Cl₂ (8 mL) was stirred at room temperature for 2 h. The solution was concentrated. The resulting residue was stirred with N-Boc-azetidin-3-one 1a (526 mg, 3.07 mmol) and Na(OAc)₃BH (651, 3.07 mmol) in 1,2-dichloroethane (8 mL) and HOAc (0.8 mL) at room temperature overnight. Additional 1a (175 mg, 1.02 mmol) and Na(OAc)₃BH (217 mg, 1.02 mmol) was added. The reaction was stirred for another 5 h before it was quenched with aq. NaHCO₃. The resulting mixture was extracted with CH₂Cl₂. The organic solution was dried over Na₂SO₄ and concentrated. Purification by column chromatography (silica gel, 6% MeOH/CH₂Cl₂) gave intermediate 2b as light yellow solid (268 mg).

Step C. 3-(2-Oxo-4-pyrimidin-2-yl-piperazin-1-yl)-azetidine-1-carboxylic acid tert-butyl ester 2c.

To a solution of intermediate 2b (210 mg, 0.72 mmol) and Et₃N (0.50 mL, 3.58 mmol) in CH₂Cl₂ (8 mL) at 0° C. was added chloroacetyl chloride (0.086 mL, 1.07 mmol). The reaction was slowly warmed up to room temperature in 3 h. It was quenched with aq. NaHCO₃ and extracted with CH₂Cl₂. The organic solution was dried over Na₂SO₄ and concentrated. To a solution of the above crude product (150 mg, 0.41 mmol) in DMF (3 mL) at 0° C. was added NaH (60% in oil, 24 mg, 0.60 mmol). The reaction was slowly warmed up to room temperature in 3 h. It was quenched with H₂O and extracted with EtOAc. The organic solution was washed with aq. NaCl, dried over Na₂SO₄ and concentrated. Purification by column chromatography (silica gel, 3% MeOH/CH₂Cl₂) gave intermediate 2c as white solid (47 mg).

Step D. Cpd 24

A solution of intermediate 2c (47 mg, 0.14 mmol) in CH₂Cl₂ (2 mL) and TFA (0.5 mL) was stirred at room temperature for 1.5 h. The reaction mixture was concentrated and the resulting residue was dissolved in CH₂Cl₂ (5 mL), and 1N HCl in ether (0.42 mL, 0.42 mmol) was added. The mixture was concentrated to give intermediate 2d, which was used in next step without further purification. A mixture of intermediate 2d (0.14 mmol), 1-(4-trifluoromethyl-phenyl)-1H-indole-5-carboxylic acid 2e (56 mg, 0.18 mmol), HATU (70 mg, 0.18 mmol), and Et₃N (0.11 mL, 0.85 mmol) in CH₂Cl₂ (3 mL) was stirred at room temperature overnight. The reaction mixture was diluted with ether and washed with aq. NaHCO₃ and aq. NaCl. The organic solution was dried over Na₂SO₄ and concentrated. Purification by column chromatography (silica gel, 3% MeOH/CH₂Cl₂) gave Cpd 24 (46 mg). MS 521 (M+H⁺).

EXAMPLE 3

1-Pyrimidin-2-yl-4-[1-({1-[4-(trifluoromethyl)phenyl]-1H-indol-5-yl}carbonyl)azetidin-3-yl]piperazin-2-one, Cpd 3

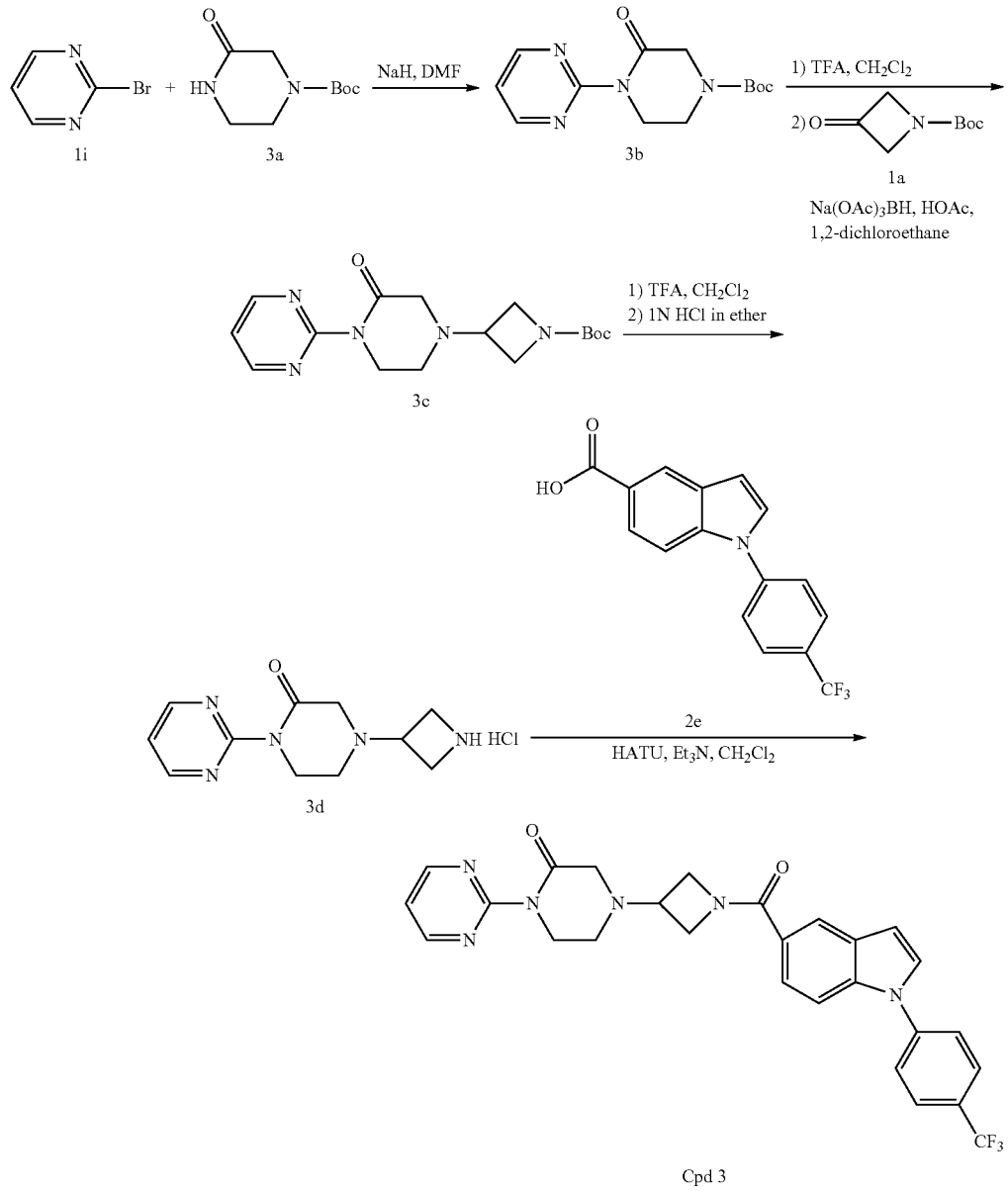

Step A. 3-Oxo-4-pyrimidin-2-yl-piperazine-1-carboxylic acid tert-butyl ester 3b.

To 1-Boc-3-oxopiperazine 3a (390 mg, 1.95 mmol) in DMF (5 mL) at 0° C. was added NaH (60% in oil, 97 mg, 2.44 mmol). The reaction was stirred at 0° C. for 25 min before a solution of 2-bromopyrimidine 1i (465 mg, 2.92 mmol) in DMF (2 mL) was added. The reaction was slowly warmed up to room temperature overnight. To the reaction mixture was added $H_2O$, and the resulting mixture was extracted with EtOAc. The organic solution was washed with aq. NaCl, dried over $Na_2SO_4$ and concentrated. Purification by column chromatography (silica gel, 3% MeOH/$CH_2Cl_2$) gave 3b as yellow oil (120 mg).

Step B. 3-(3-Oxo-4-pyrimidin-2-yl-piperazin-1-yl)-azetidine-1-carboxylic acid tert-butyl ester 3c.

A solution of intermediate 3b (120 mg, 0.43 mmol) in TFA (0.75 mL) and $CH_2Cl_2$ (3 mL) was stirred at room temperature for 1.5 h. The solution was concentrated. The resulting residue was stirred with N-Boc-azetidin-3-one 1a (81 mg, 0.47 mmol) and Na(OAc)$_3$BH (100, 0.47 mmol) in 1,2-dichloroethane (4 mL) and HOAc (0.2 mL) at room temperature overnight. The reaction was quenched with aq. NaHCO$_3$. The resulting mixture was extracted with $CH_2Cl_2$. The organic solution was dried over $Na_2SO_4$ and concentrated. Purification by column chromatography (silica gel, 3% MeOH/$CH_2Cl_2$) gave intermediate 3c as light yellow solid (15 mg).

Step C. Cpd 3

Cpd 3 was prepared according to the procedures described in Example 2, Step D, using intermediates 3c and 2e as starting materials. MS 521 (M+H$^+$).

The following compounds were prepared using the procedures described in Example 3, except using commercially available 1-phenyl-piperazin-2-one as starting material.

| Cpd | Name and data |
|---|---|
| 1 | 4-(1-(4-benzylbenzoyl)azetidin-3-yl)-1-phenylpiperazin-2-one<br>MS 426 (M + H⁺) |
| 2 | 4-(1-([1,1'-biphenyl]-4-carbonyl)azetidin-3-yl)-1-phenylpiperazin-2-one<br>MS 412 (M + H⁺) |
| 13 | 1-Phenyl-4-[1-({1-[4-(trifluoromethyl)phenyl]-1H-indol-5-yl}carbonyl)azetidin-3-yl]piperazin-2-one<br>MS 519 (M + H⁺). |
| 15 | 4-(1-{[1-(3,4-Difluorophenyl)-1H-indol-5-yl]carbonyl}azetidin-3-yl)-1-phenylpiperazin-2-one<br>MS 487 (M + H⁺). |

EXAMPLE 3a

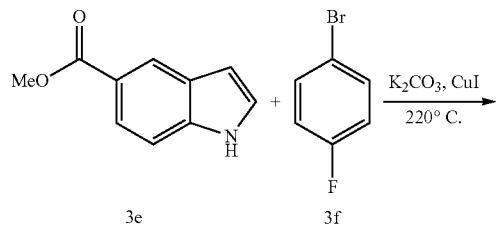

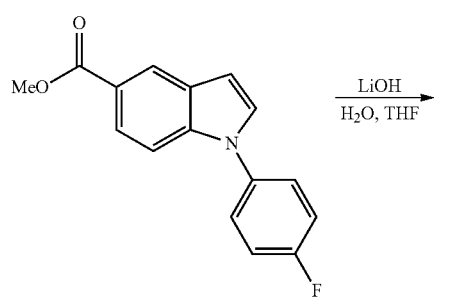

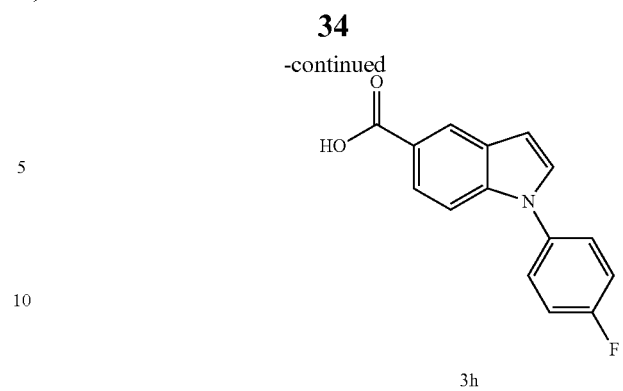

3h

A. Methyl 1-(4-fluorophenyl)-indole-5-carboxylate, 3g. A mixture of methyl indole-5-carboxylate 3e (0.5 g, 2.85 mmol), 1-bromo-4-fluoro-benzene 3f (2 mL, 18.21 mmol), CuI (0.544 g, 2.85 mmol), and $K_2CO_3$ (0.591 g, 4.28 mmol) was heated under microwave at 220° C. for 2.5 hours. The reaction mixture was diluted with $CH_2Cl_2$ and filtered. The solution was concentrated and the residue was purified by flash column chromatography (silica gel, 15% EtOAc/heptane) to give 3 g (0.58 g).

I. 1-(4-fluorophenyl)-indole-5-carboxylic acid, 3h. A mixture of methyl 1-(4-fluorophenyl)-indole-5-carboxylate 3g (0.58 g, 2.15 mmol) and LiOH·$H_2O$ (0.36 g, 8.6 mmol) in THF (15 mL) and $H_2O$ (10 mL) was stirred at room temperature for 5 days. Aqueous 10% HCl solution was added to the reaction mixture to adjust pH=3~4. The resulting mixture was extracted with EtOAc (2×). The organic solution was washed with aq. NaCl, dried over $Na_2SO_4$ and concentrated to give 3h (0.5 g).

Following the procedure described above for Example 3a and substituting the appropriate reagents, starting materials, and purification methods known to those skilled in the art, the following intermediate was prepared:

Cpd 2e

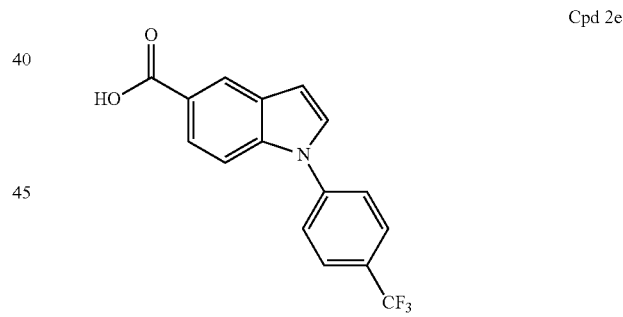

EXAMPLE 4

4-(1-{[1-(4-Fluorophenyl)-1H-indol-5-yl]carbonyl}azetidin-3-yl)-1-pyrimidin-2-ylpiperazin-2-one, Cpd 4

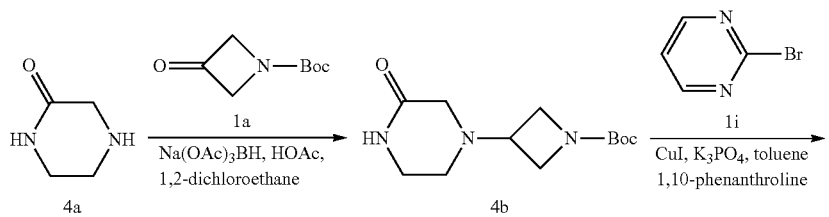

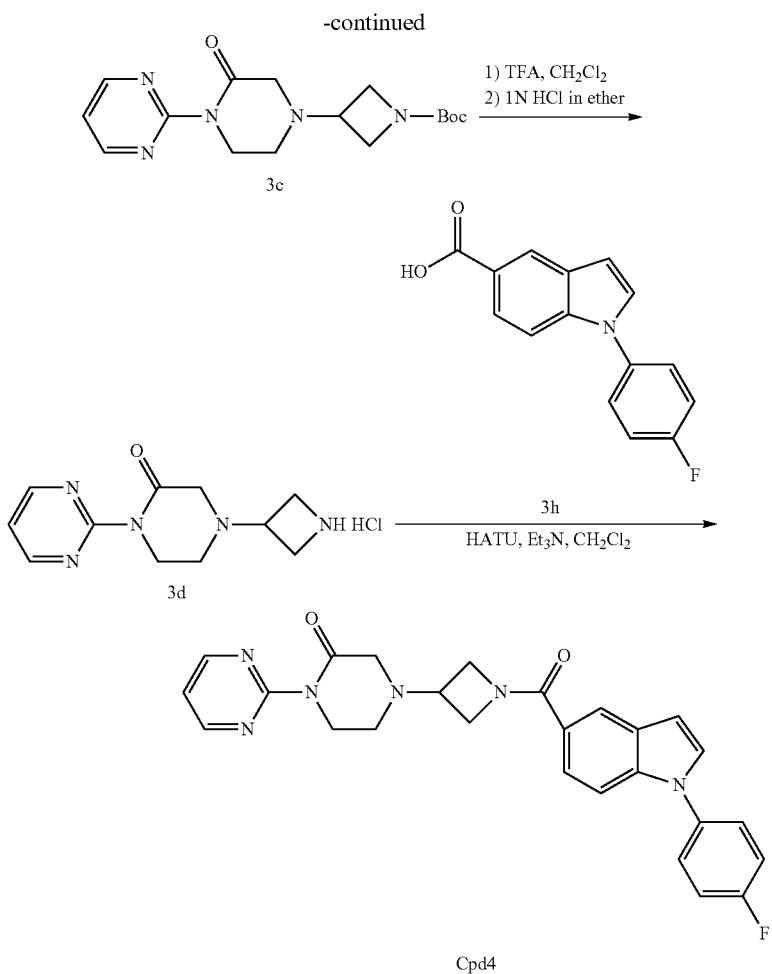

Step A. 3-(3-Oxo-piperazin-1-yl)-azetidine-1-carboxylic acid tert-butyl ester 4b.

To a mixture of 3-oxopiperazine 4a (490 mg, 4.89 mmol) and N-Boc-azetidin-3-one 1a (922 mg, 5.38 mmol) in 1,2-dichloroethane (10 mL) and HOAc (0.5 mL) was added Na(OAc)$_3$BH (1141, 5.38 mmol). The reaction was stirred at room temperature overnight. Additional 1a (335 mg, 1.96 mmol) and Na(OAc)$_3$BH (415 mg, 1.96 mmol) was added. The reaction was stirred for another 24 h before it was quenched with aq. NaHCO$_3$. The resulting mixture was extracted with CH$_2$Cl$_2$. The organic solution was dried over Na$_2$SO$_4$ and concentrated. Purification by column chromatography (silica gel, 4% MeOH/CH$_2$Cl$_2$) gave intermediate 4b as white solid (860 mg).

Step B. 3-(3-Oxo-4-pyrimidin-2-yl-piperazin-1-yl)-azetidine-1-carboxylic acid tert-butyl ester 3c.

A mixture of intermediate 4b (52 mg, 0.204 mmol), 2-bromopyrimidine 1i (65 mg, 0.41 mmol), CuI (8 mg, 0.04 mmol), 1,10-phenanthroline (18 mg, 0.10 mmol), and K$_3$PO$_4$ (95 mg, 0.45 mmol) in toluene (1 mL) was heated at 110° C. under N$_2$ for 9 h. The reaction mixture was diluted with CH$_2$Cl$_2$ and filtered. The solution was concentrated and purification by column chromatography (silica gel, 3% MeOH/CH$_2$Cl$_2$) gave intermediate 3c as light yellow solid (25 mg).

Step C. Cpd 4

Cpd 4 was prepared according to the procedures described in Example 2, Step D, using intermediates 3c and 1-(4-fluorophenyl)-1H-indole-5-carboxylic acid 3h as starting materials. MS 471 (M+H$^+$).

The following compounds were prepared following the procedures described in Example 4.

| Cpd | Name and data |
|---|---|
| 5 | 4-(1-{[1-(4-Fluorophenyl)-1H-indol-5-yl]carbonyl}azetidin-3-yl)-1-(1,3-thiazol-2-yl)piperazin-2-one<br>MS 476 (M + H$^+$). |
| 6 | 4-(1-{[1-(4-Fluorophenyl)-1H-indol-5-yl]carbonyl}azetidin-3-yl)-1-(1,3-thiazol-4-yl)piperazin-2-one<br>MS 476 (M + H$^+$). |
| 9 | 4-[1-(Biphenyl-4-ylcarbonyl)azetidin-3-yl]-1-pyrimidin-2-ylpiperazin-2-one<br>MS 414 (M + H$^+$). |
| 10 | 4-{1-[(2-Phenyl-1,3-benzothiazol-6-yl)carbonyl]azetidin-3-yl}-1-pyrimidin-2-ylpiperazin-2-one<br>MS 471 (M + H$^+$). |
| 12 | 4-{1-[(2-Phenyl-1,3-benzothiazol-6-yl)carbonyl]azetidin-3-yl}-1-(1,3-thiazol-2-yl)piperazin-2-one<br>MS 476 (M + H$^+$). |
| 16 | 4-{1-[(2-Phenyl-1,3-benzoxazol-6-yl)carbonyl]azetidin-3-yl}-1-(1,3-thiazol-2-yl)piperazin-2-one<br>MS 460 (M + H$^+$). |
| 18 | 4-[1-(Biphenyl-4-ylcarbonyl)azetidin-3-yl]-1-(1,3-thiazol-2-yl)piperazin-2-one<br>MS 419 (M + H$^+$). |

-continued

| Cpd | Name and data |
|---|---|
| 20 | 1-(1-{[1-(4-Fluorophenyl)-1H-indol-5-yl]carbonyl}azetidin-3-yl)-4-pyrimidin-2-yl-1,4-diazepan-5-one<br>MS 485 (M + H+). |
| 21 | 1-(1-{[1-(4-Fluorophenyl)-1H-indol-5-yl]carbonyl}azetidin-3-yl)-4-(1,3-thiazol-2-yl)-1,4-diazepan-5-one<br>$^1$H NMR (CHLOROFORM-d, 400 MHz): δ = 7.99 (s, 1 H), 7.39-7.66 (m, 5 H), 7.34 (d, J = 3.5 Hz, 1 H), 7.15-7.31 (m, 2 H), 7.01 (d, J = 3.5 Hz, 1 H), 6.74 (d, J = 3.1 Hz, 1 H), 4.64 (br. s., 2 H), 4.00-4.47 (m, 4 H), 3.33 (dt, J = 12.3, 6.4 Hz, 1 H), 3.00 (br. s., 2 H), 2.46-2.86 ppm (m, 4 H). MS 490 (M + H+). |
| 22 | 1-{1-[(2-Phenyl-1,3-benzoxazol-6-yl)carbonyl]azetidin-3-yl}-4-(1,3-thiazol-2-yl)-1,4-diazepan-5-one<br>$^1$H NMR (CHLOROFORM-d, 400 MHz): δ = 8.28 (d, J = 6.7 Hz, 2 H), 7.92 (s, 1 H), 7.79 (d, J = 8.2 Hz, 1 H), 7.66 (d, J = 8.2 Hz, 1 H), 7.51-7.62 (m, 3 H), 7.47 (d, J = 3.1 Hz, 1 H), 7.02 (d, J = 3.1 Hz, 1 H), 4.66 (br. s., 2 H), 3.95-4.51 (m, 4 H), 3.24-3.44 (m, 1 H), 3.02 (br. s., 2 H), 2.42-2.87 ppm (m, 4 H). MS 474 (M + H+). |

EXAMPLE 5

4-(1-{[3-Chloro-6-(trifluoromethyl)-1-benzothiophen-2-yl]carbonyl}azetidin-3-yl)-1-pyrimidin-2-ylpiperazin-2-one, Cpd 8

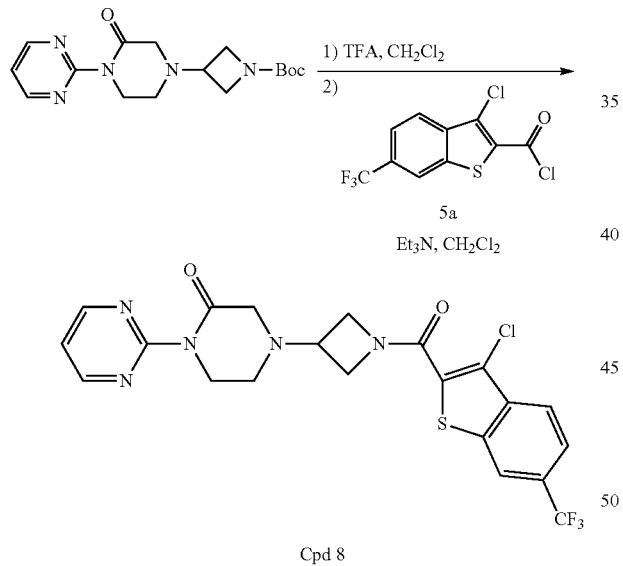

Cpd 8

A solution of intermediate 3c (prepared by procedures described in Example 4) in CH$_2$Cl$_2$ (2 mL) and TFA (0.5 mL) was stirred at room temperature for 1h. The solution was concentrated, and the residue was dissolved in CH$_2$Cl$_2$ (2.5 mL). To the resulting solution at 0° C. was added Et$_3$N (0.11 mL, 0.79 mmol), followed by a solution of 3-chloro-6-trifluoromethyl-benzo[b]thiophene-2-carbonyl chloride 5a (prepared from 3-chloro-6-trifluoromethyl-benzo[b]thiophene-2-carboxylic acid following the procedures described in Example 1, Step A) (0.14 mmol) in CH$_2$Cl$_2$ (1.5 mL). The reaction was slowly warmed up to room temperature in 2 h, and was then quenched with aq. NaHCO$_3$. The mixture was extracted with CH$_2$Cl$_2$. The organic solution was dried over Na$_2$SO$_4$ and concentrated. Purification by column chromatography (silica gel, 3% MeOH/CH$_2$Cl$_2$) gave Cpd 8 as yellow solid (28 mg). MS 496 (M+H+).

The following compounds were prepared following the procedures described in Example 5.

| Cpd | Name and data |
|---|---|
| 7 | 4-(1-{[3-Chloro-6-(trifluoromethyl)-1-benzothiophen-2-yl]carbonyl}azetidin-3-yl)-1-(1,3-thiazol-4-yl)piperazin-2-one<br>MS 501 (M + H+). |
| 11 | 4-(1-{[3-Chloro-6-(trifluoromethyl)-1-benzothiophen-2-yl]carbonyl}azetidin-3-yl)-1-(1,3-thiazol-2-yl)piperazin-2-one<br>$^1$H NMR (CHLOROFORM-d, 400 MHz): δ = 8.13 (br. s., 1 H), 8.02 (d, J = 7.8 Hz, 1 H), 7.73 (d, J = 7.8 Hz, 1 H), 7.53 (br. s., 1 H), 7.06 (d, J = 3.1 Hz, 1 H), 3.99-4.60 (m, 6 H), 3.20-3.50 (m, 3 H), 2.65-3.00 ppm (m, 2 H).<br>MS 501 (M + H+). |
| 17 | 1-(1-{[3-Chloro-6-(trifluoromethyl)-1-benzothiophen-2-yl]carbonyl}azetidin-3-yl)-4-pyrimidin-2-yl-1,4-diazepan-5-one<br>MS 510 (M + H+). |
| 19 | 1-(1-{[3-Chloro-6-(trifluoromethyl)-1-benzothiophen-2-yl]carbonyl}azetidin-3-yl)-4-(1,3-thiazol-2-yl)-1,4-diazepan-5-one<br>$^1$H NMR (CHLOROFORM-d, 400 MHz): δ = 8.13 (s, 1 H), 7.98-8.07 (m, 1 H), 7.73 (d, J = 8.6 Hz, 1 H), 7.47 (d, J = 3.5 Hz, 1 H), 7.02 (d, J = 3.5 Hz, 1 H), 4.67 (br. s., 2 H), 4.28-4.42 (m, 2 H), 4.13 (d, J = 14.1 Hz, 2 H), 3.32-3.50 (m, 1 H), 2.95-3.09 (m, 2 H), 2.64 ppm (d, 4 H). MS 515 (M + H+). |

EXAMPLE 6

4-(1-{[3-Chloro-6-(trifluoromethyl)-1-benzothiophen-2-yl]carbonyl}azetidin-3-yl)-1-phenylpiperazin-2-one, Cpd 14

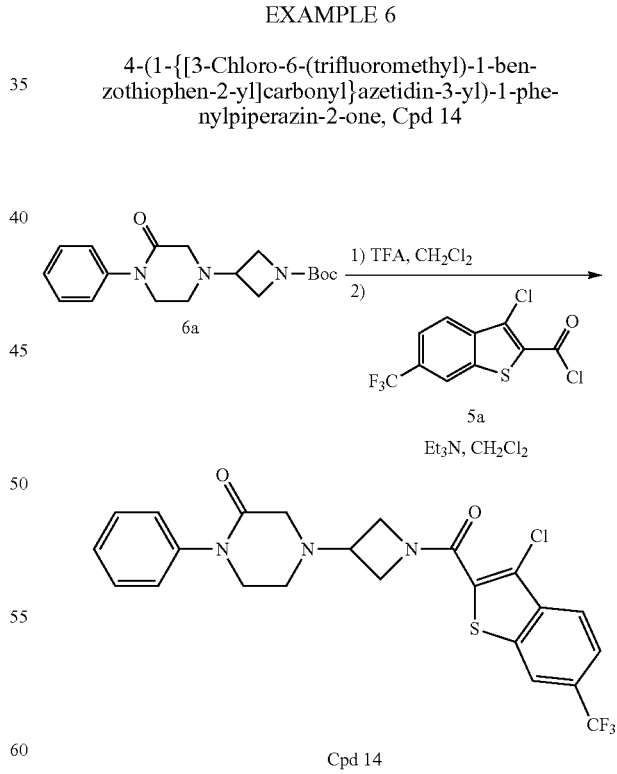

Cpd 14

Cpd 14 was prepared following the procedures described in Example 5 with intermediates 6a and 5a. Intermediate 6a was prepared following the procedures described in Example 3, Step B, using commercially available 1-phenyl-piperazin-2-one as starting material. MS 494 (M+H+).

Examples 7-26 provide synthetic routes to useful intermediates for the preparation of compounds of Formula (I).

EXAMPLE 7

EXAMPLE 8

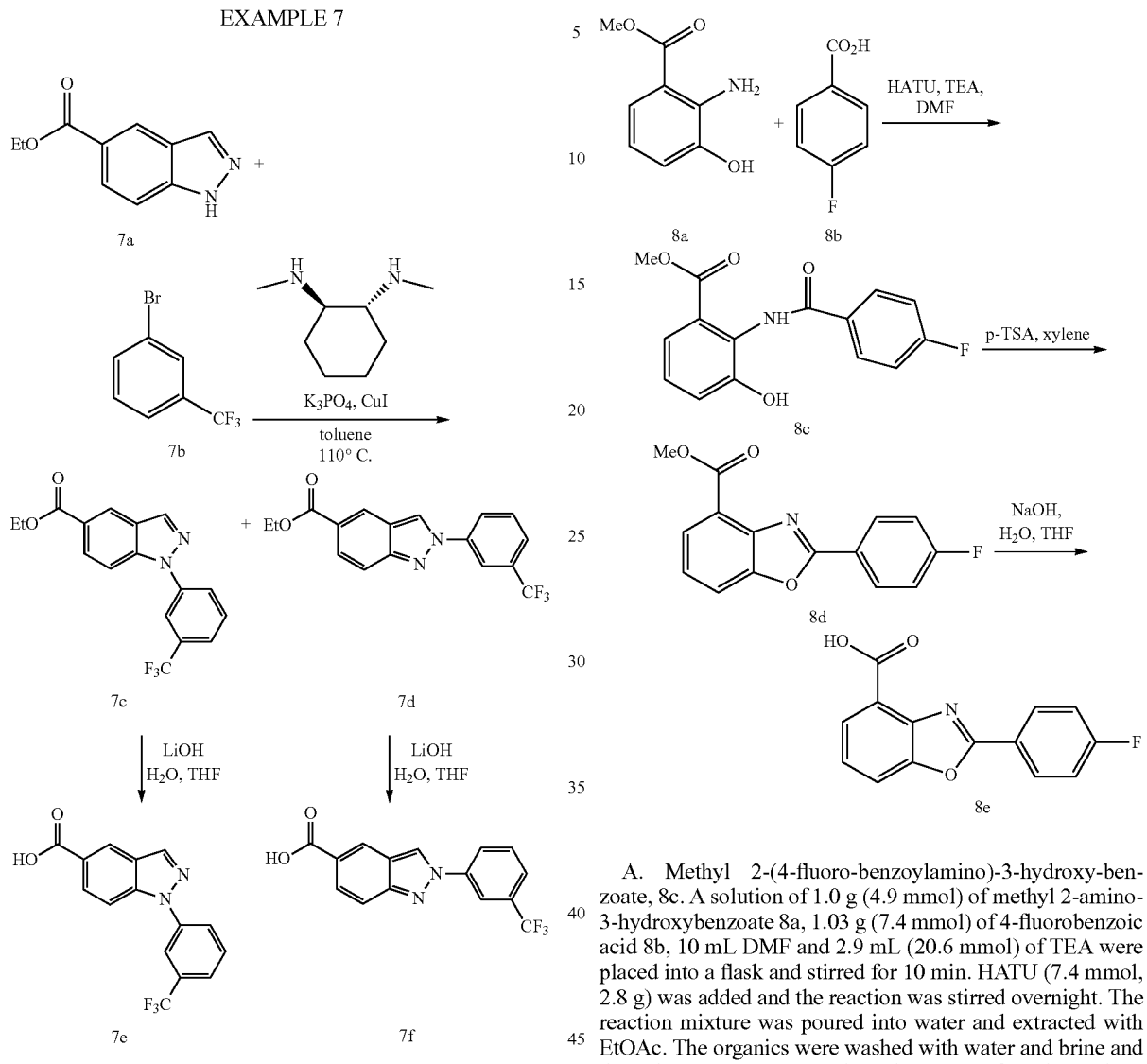

A. Ethyl 1-(3-trifluoromethyl-phenyl)-1H-indazole-5-carboxylate, 7c and Ethyl 2-(3-trifluoromethyl-phenyl)-2H-indazole-5-carboxylate, 7d. A mixture of ethyl 1H-Indazole-5-carboxylate 7a (150 mg, 0.79 mmol), 1-bromo-3-trifluoromethylbenzene 7b (0.13 mL, 0.95 mmol), CuI (22.5 mg, 0.12 mmol), trans-N,N'-dimethylcyclohexane-1,2-diamine (0.056 mL, 0.36 mmol), and $K_3PO_4$ (0.37 g, 1.74 mmol) in toluene (1.5 mL) was heated at 110° C. for 16 hours. The reaction mixture was diluted with $CH_2Cl_2$ and filtered. The solution was concentrated and the residue was purified by flash column chromatography (silica gel, 10% EtOAc/heptane) to give 7c (190 mg), followed by 7d (37 mg).

B. 1-(3-Trifluoromethyl-phenyl)-1H-indazole-5-carboxylic acid, 7e and 2-(3-Trifluoromethyl-phenyl)-2H-indazole-5-carboxylic acid, 7f. A mixture of 7c and 7d and LiOH in THF (120 mL) and $H_2O$ (60 mL) was stirred at room temperature for 5 days. Aqueous 10% HCl solution was added to the reaction mixture to adjust pH=3~4. The resulting mixture was extracted with EtOAc (2×). The organic solution was washed with aq. NaCl, dried over $Na_2SO_4$ and concentrated to give 7e and 7f.

A. Methyl 2-(4-fluoro-benzoylamino)-3-hydroxy-benzoate, 8c. A solution of 1.0 g (4.9 mmol) of methyl 2-amino-3-hydroxybenzoate 8a, 1.03 g (7.4 mmol) of 4-fluorobenzoic acid 8b, 10 mL DMF and 2.9 mL (20.6 mmol) of TEA were placed into a flask and stirred for 10 min. HATU (7.4 mmol, 2.8 g) was added and the reaction was stirred overnight. The reaction mixture was poured into water and extracted with EtOAc. The organics were washed with water and brine and the solvent was evaporated to give 1.2 g of crude product, methyl 2-(4-fluoro-benzoylamino)-3-hydroxy-benzoate, 8c, which was used without purification. MS m/z (M+H⁺) 290.1.

B. Methyl 2-(4-fluorophenyl)benzo[d]oxazole-4-carboxylate, 8d. Methyl 2-(4-fluoro-benzoylamino)-3-hydroxy-benzoate 8c (7.4 mmol, 1.2 g crude) and 1.3 g (7.5 mmol) of p-toluenesulfonic acid were refluxed in 10 mL of xylene overnight. After cooling saturated $NaHCO_3$ was added and the resulting mixture was extracted with EtOAc. The organic solvent was evaporated to give 1.1 g (55%) of methyl 2-(4-fluorophenyl)benzo[d]oxazole-4-carboxylate, 8d. MS m/z (M+H⁺) 272.0.

C. 2-(4-Fluorophenyl)-benzo[d]oxazole-4-carboxylic acid, 8e. A mixture of 1.1 g (4.0 mmol) methyl 2-(4-fluorophenyl)benzo[d]oxazole-4-carboxylate 8d and 3.7 mL of 3N aqueous NaOH in 10 mL of THF was refluxed overnight. After cooling the reaction mixture was poured into water and acidified with conc. HCl. The resulting solid was filtered and dried to give 830 mg (79%) of 2-(4-fluorophenyl)-benzo[d]oxazole-4-carboxylic acid, 8e. MS m/z (M+H⁺) 258.1.

Following the procedure described above for Example 8, and substituting the appropriate reagents, starting materials, and purification methods known to those skilled in the art, the following intermediate compounds were prepared:
8-I1
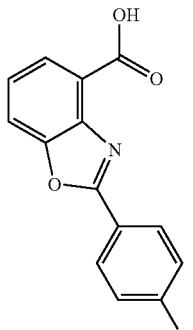
8-I2
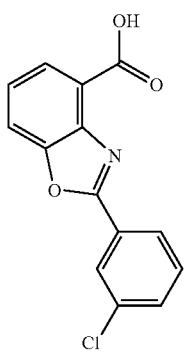
8-I3
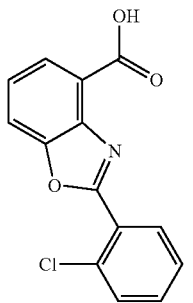
8-I4
8-I5
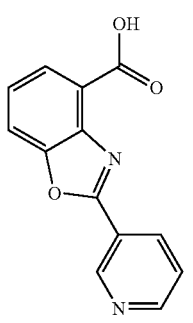
8-I6
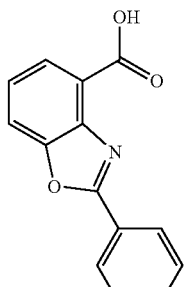
8-I7
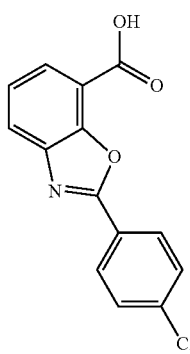
8-I8
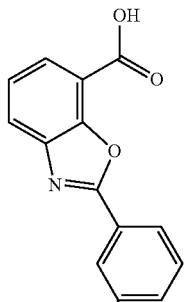
8-I9
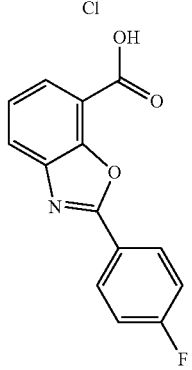
8-I10
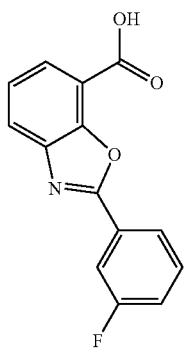

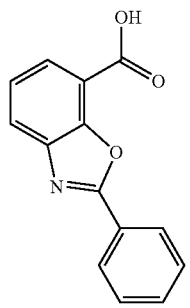

8-I11

EXAMPLE 9

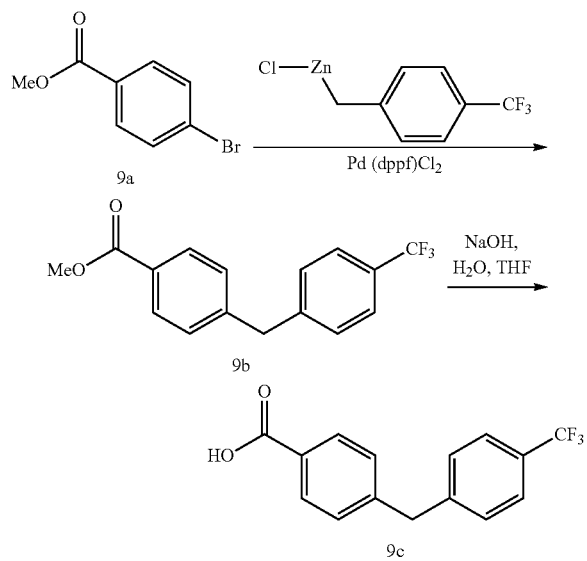

A. Methyl 4-(4-(trifluoromethyl)benzyl)benzoate, 9b. Argon was bubbled through a mixture of methyl 4-bromobenzoate 9a (9.3 mmol, 2.0 g), 2 mL of THF, and 4-trifluoromethylbenzylzinc chloride (0.5 M in THF, 46.5 mmol, 93 mL) for 5 min. Pd(dffp)Cl$_2$.CH$_2$Cl$_2$ (0.5 mol, 409 mg) was added and the reaction tube was capped and heated at 70° C. for 16 h. The mixture was cooled and filtered through diatomaceous earth. Water was added to the filtrate and the resulting solid was filtered off. The organic solution was dried over MgSO$_4$ and concentrated. The crude product was purified by flash chromatography (silica gel, 0-10% EtOAc in heptane) to give 1.5 g (55%) of methyl 4-(4-(trifluoromethyl)benzyl)benzoate, 9b.

B. 4-(4-(Trifluoromethyl)benzyl)benzoic acid, 9c. A mixture of methyl 4-(4-(trifluoromethyl)benzyl)benzoate 9b (1.5 g, 5.1 mmol) and 3N aqueous NaOH was refluxed in 8 mL of THF overnight. After cooling, the mixture was poured into ice water and acidified with conc. HCl. The resulting solid was filtered and dried to give methyl 1.31 g (92%) of 4-(4-(trifluoromethyl)benzyl)benzoic acid, 9c. MS m/z (M+H$^+$) 279.1.

Intermediate compounds were optionally prepared by an alternative procedure:

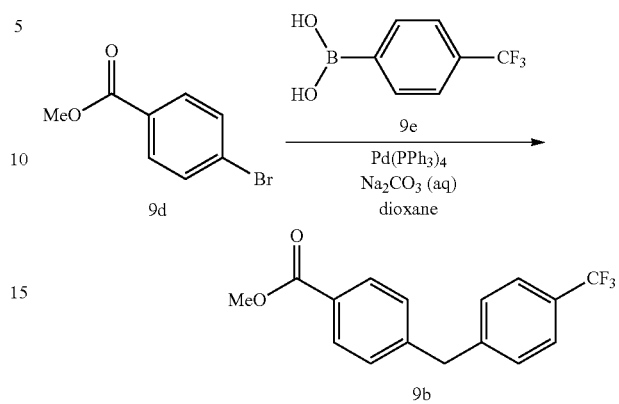

Methyl 4-(4-(trifluoromethyl)benzyl)benzoate, 9b. A mixture of 4-bromomethyl-benzoic acid methyl ester 9d (1.0 g, 4.37 mmol), 4-trifluorophenyl boronic acid 9e (0.995 g, 5.24 mmol), and Pd(PPh$_3$)$_4$ (50 mg, 0.044 mmol) in dioxane (15 mL) was stirred at room temperature for 1 min. Next, 4 mL of 2 M aqueous Na$_2$CO$_3$ solution was added. The resulting solution was heated at 90° C. for 5 h and was then cooled to rt. EtOAc and water were added to the reaction mixture. The organics were concentrated and purified by flash chromatography (silica gel, 5% EtOAc/hexanes) to give methyl 4-(4-(trifluoromethyl)benzyl)benzoate, 9b.

EXAMPLE 10

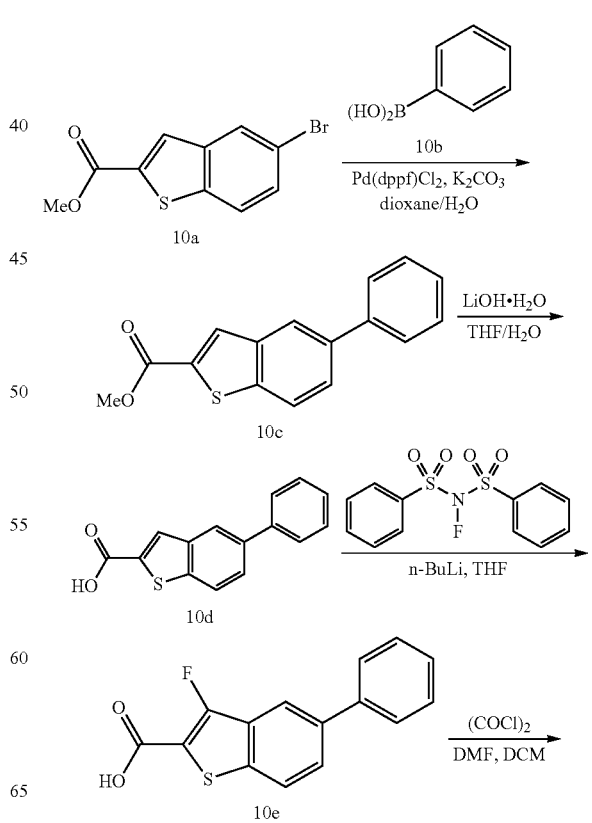

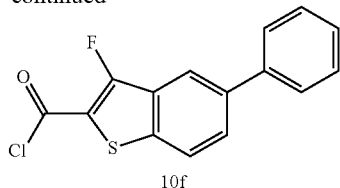

A. Methyl 5-phenyl-benzo[b]thiophene-2-carboxylate, 10c. A mixture of compound 10a (542.3 mg, 2 mmol), phenyl boronic acid 10b (268.2 mg, 2.2 mmol), Pd(dppf)Cl$_2$·CH$_2$Cl$_2$ (98 mg, 0.12 mmol), and K$_2$CO$_3$ (414.6 mg, 3 mmol), in a dioxane (4 mL)/water (1 mL) mixture, was placed in a capped vial and heated at 80° C. overnight. The reaction mixture was then diluted with EtOAc and water. The organic layer was concentrated under reduced pressure and purified by flash column chromatography (silica gel, 2-10% EtOAc/heptane) to give compound 10c (510 mg). MS m/z (M+H$^+$) 269.1.

B. 5-Phenyl-benzo[b]thiophene-2-carboxylic acid, 10d. A solution of compound 10c (510 mg, 1.9 mmol) and LiOH·H$_2$O (319 mg, 7.6 mmol) in THF/H$_2$O (10/10 mL) was stirred at room temperature overnight. The resulting mixture was concentrated and diluted with water. The water layer was acidified with 1N aqueous HCl to pH~4 and extracted with CH$_2$Cl$_2$. The organic solution was dried over Na$_2$SO$_4$ and concentrated to give 10d (479 mg), which was used in the next reaction without further purification. MS m/z (M+H$^+$) 255.0.

C. 3-Fluoro-5-phenyl-benzo[b]thiophene-2-carboxylic acid, 10e. To a solution of compound 10d (507 mg, 1.99 mmol) in THF (8 mL) at −70° C. was added n-BuLi (1.6 M in hexane, 2.62 mL, 4.19 mmol). The mixture was stirred at −70° C. for 1 h; then a solution of N-fluorobenzenesulfonimide (817.3 mg, 2.59 mmol) in THF (2 mL) was slowly added. The reaction mixture was allowed to warm to room temperature and was stirred overnight. The resulting mixture was partitioned between dilute aqueous HCl and EtOAc. The organic solution was washed with water and brine, dried over Na$_2$SO$_4$, and concentrated. The residue was tritiated with CH$_2$Cl$_2$, filtered and the solid dried to give compound 10e (391.9 mg). MS m/z (M+H$^+$) 273.0.

D. 3-Fluoro-5-phenyl-benzo[b]thiophene-2-carbonyl chloride, 10f. To a solution of compound 10e (136.2 mg, 0.5 mmol) in CH$_2$Cl$_2$ (5 mL) at room temperature was added (COCl)$_2$ (0.064 mL, 0.75 mmol), followed by DMF (0.01 mL, 0.125 mmol). The reaction mixture was stirred at room temperature for 18 h. The reaction mixture was then concentrated to give compound 10f (light pink powder).

EXAMPLE 11

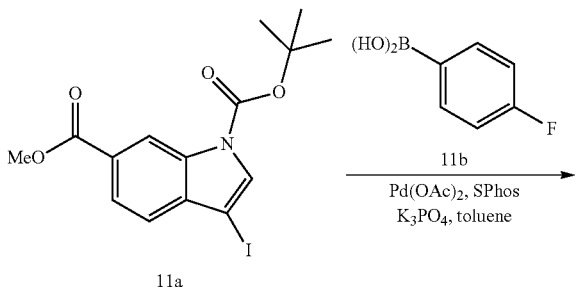

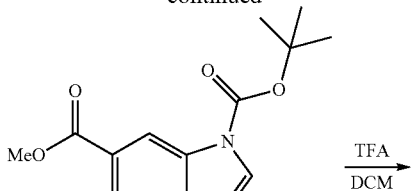

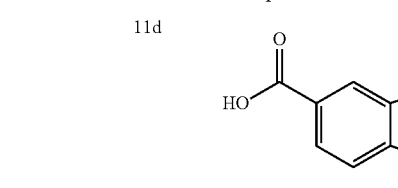

A. 1-tert-Butyl 6-methyl 3-(4-fluorophenyl)-1H-indole-1,6-dicarboxylate, 11c. A mixture of compound 11a (1.00 g, 2.49 mmol), 4-fluorophenyl boronic acid 11b (523 mg, 3.74 mmol), Pd(OAc)$_2$ (44.8 mg, 0.2 mmol), 2-dicyclohexylphosphino-2',6'-dimethoxybiphenyl (SPhos, 204.7 mg, 0.5 mmol), and K$_3$PO$_4$ (1.06 g, 4.99 mmol), in toluene (5 mL) was placed in a capped vial and heated at 90° C. under N$_2$ for 3 h. The reaction mixture was then diluted with EtOAc and water. The organic layer was washed with brine, concentrated under reduced pressure, and purified by flash column chromatography (silica gel, 2-10% EtOAc/heptane) to give compound 11c as a light yellow solid, which was further recrystallized from heptane to obtain white solid (707 mg). MS m/z (M+H$^+$) 370.2.

B. Methyl 3-(4-fluorophenyl)-1H-indole-6-carboxylate, 11d. To a solution of compound 11c (705 mg, 1.91 mmol) in CH$_2$Cl$_2$ (4 mL) was added trifluoroacetic acid (1.5 mL) at room temperature. The mixture was stirred at room temperature for 2 h. The resulting mixture was concentrated to give compound 11d (603.3 mg) as a white solid. MS m/z (M+H$^+$) 270.1.

C. 3-(4-Fluoro-phenyl)-1H-indole-6-carboxylic acid, 11e. A solution of compound 11d (303 mg, 0.79 mmol), and LiOH·H$_2$O (132.7 mg, 3.16 mmol) in THF/H$_2$O (10 mL/10 mL) was stirred at 45° C. for 5 h. The resulting mixture was concentrated and diluted with water. The water layer was acidified with 1N aqueous HCl to pH~4 and extracted with CH₂Cl₂. The organic solution was dried over Na₂SO₄ and concentrated to give 11e (249 mg). MS m/z (M+H⁺) 256.0.

Following the procedure described above for Example 11, and substituting the appropriate reagents, starting materials and purification methods known to those skilled in the art, the following intermediate compounds were prepared:

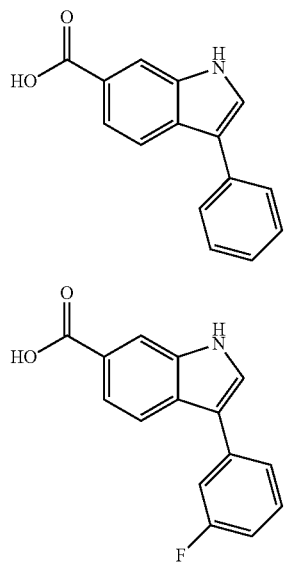

11-I1

11-I2

EXAMPLE 12

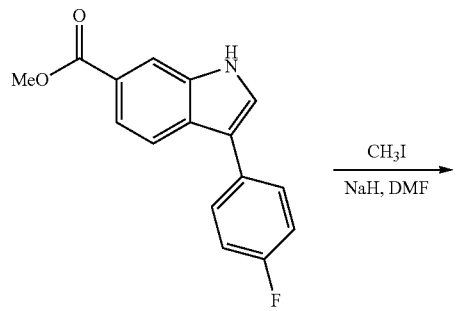

11d

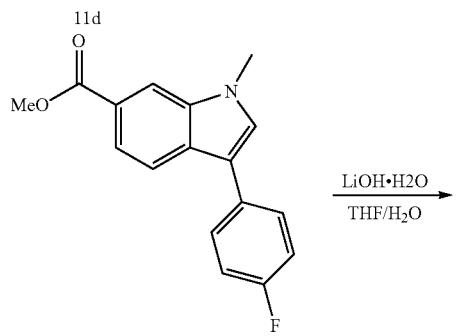

12a

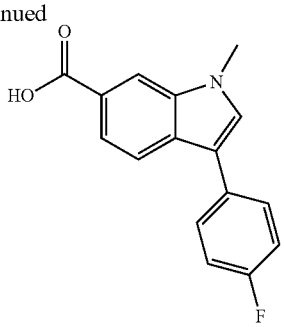

12b

A. Methyl 3-(4-fluoro-phenyl)-1-methyl-1H-indole-6-carboxylate, 12a. To a solution of compound 11d (300 mg, 0.78 mmol) in DMF (3 mL) was added NaH (60% in mineral oil, 68.9 mg, 1.72 mmol) at 0° C. The mixture was stirred at 0° C. for 30 min, then CH₃I (0.053 mL, 0.86 mmol) was added and stirring continued at 0° C. for another 1 h. The resulting mixture was diluted with EtOAc and water. The organic layer was washed with brine and concentrated. The residue was recrystallized from heptane, filtered and the solid dried to give compound 12a (265 mg) as a light yellow solid. MS m/z (M+H⁺) 284.1.

B. 3-(4-Fluoro-phenyl)-1-methyl-1H-indole-6-carboxylic acid, 12b. To a solution of compound 12a (264 mg, 0.93 mmol), and LiOH·H₂O (156.4 mg, 3.73 mmol) in THF/H₂O (10 mL/10 mL) was stirred at 45° C. for 5 h. The resulting mixture was concentrated and diluted with water. The water layer was acidified with 1N aqueous HCl to pH~4 and extracted with CH₂Cl₂. The organic solution was dried over Na₂SO₄ and concentrated to give compound 12b (252 mg). MS m/z (M+H⁺) 270.1.

Following the procedure described above for Example 12 and substituting the appropriate reagents, starting materials and purification methods known to those skilled in the art, the following intermediate compound was prepared:

12-I1

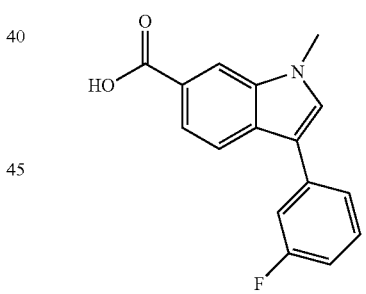

EXAMPLE 13

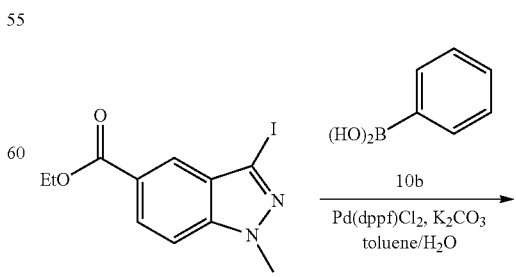

13a

EXAMPLE 14

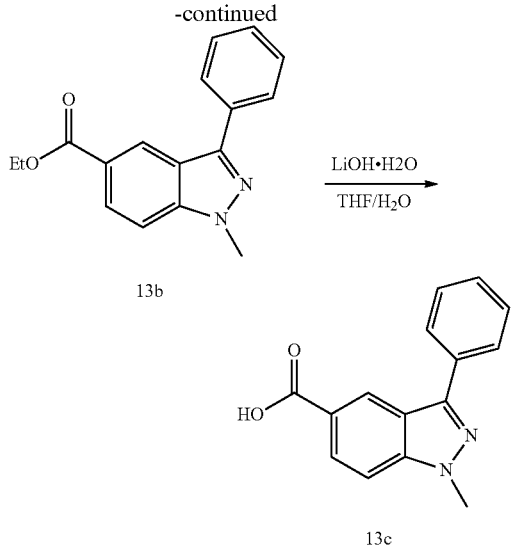

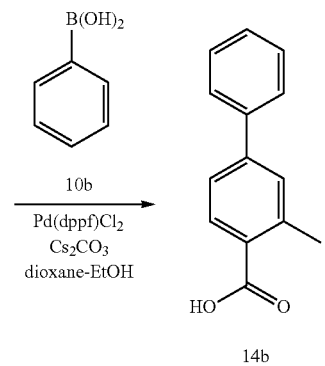

A. 3-Methyl-[1,1'-biphenyl]-4-carboxylic acid, 14b. To a suspension of compound 14a (0.025 g, 0.115 mmol), compound 10b (0.0139 g, 0.14 mmol), and $Cs_2CO_3$ (0.094 g, 0.288 mmol) in dioxane (3 mL) and EtOH (1 mL) was added Pd(dppf)Cl$_2$ (0.0084 g, 0.0115 mmol). The reaction mixture was stirred at 80° C. for 3 h. After cooling, the solid was removed by filtration and washed with $CH_3OH$. The filtrate was concentrated. The crude product 14b was purified by reverse phase chromatography. MS m/z (M+H$^+$) 213.1.

A. Ethyl 1-Methyl-3-phenyl-1H-indazole-5-carboxylate, 13b. A mixture of compound 13a (300 mg, 0.91 mmol), phenyl boronic acid 10b (133 mg, 1.09 mmol), Pd(dppf)Cl$_2$.CH$_2$Cl$_2$ (40 mg, 0.055 mmol), and $K_2CO_3$ (251.2 mg, 1.82 mmol), in a toluene (2 mL)/water (0.4 mL) mixture, was placed in a capped vial and heated at 90° C. overnight. The reaction mixture was then diluted with EtOAc and water. The organic layer was concentrated under reduced pressure and purified by flash column chromatography (silica gel, 2-10% EtOAc/Heptanes) to give compound 13b (231 mg). MS m/z (M+H$^+$) 281.1.

B. 1-Methyl-3-phenyl-1H-indazole-5-carboxylic acid, 13c. A solution compound 13b (230 mg, 0.58 mmol), and LiOH.H$_2$O (98 mg, 2.33 mmol) in THF/H$_2$O (10/10 mL) was stirred at 45° C. for 8 h. The resulting mixture was concentrated and diluted with water. The water layer was acidified with 1N aqueous HCl to pH~4 and extracted with CH$_2$Cl$_2$. The organic solution was dried over Na$_2$SO$_4$ and concentrated to give 13c (206 mg). MS m/z (M+H$^+$) 253.1.

Following the procedure described above for Example 13 and substituting the appropriate reagents, starting materials and purification methods known to those skilled in the art, the following intermediate compounds were prepared:

13-I1

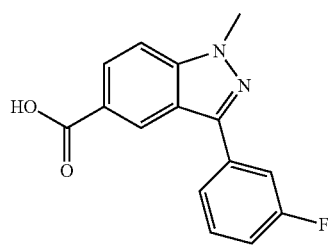

13-I2

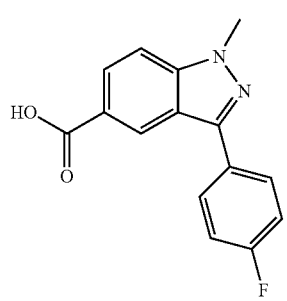

Following the procedure described above for Example 14 and substituting the appropriate reagents, starting materials and purification methods known to those skilled in the art, the following intermediate compounds were prepared:

14-I1

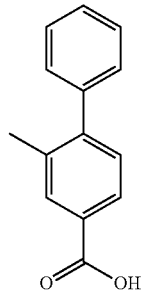

14-I2

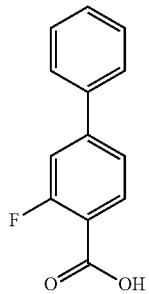

14-I3

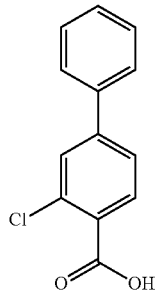

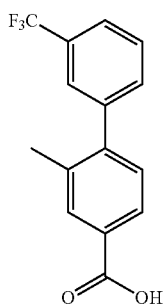
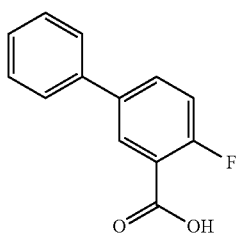
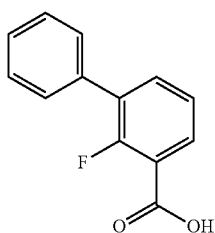
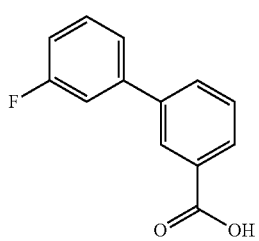
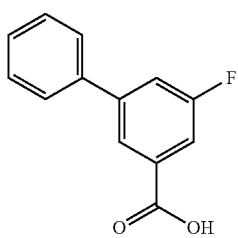
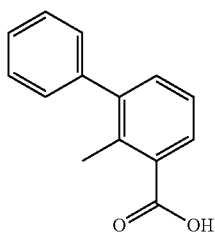
14-I4
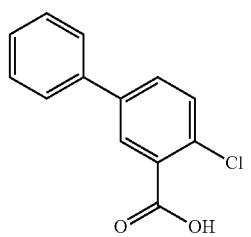
14-I5
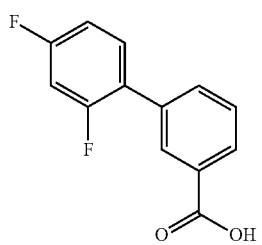
14-I6
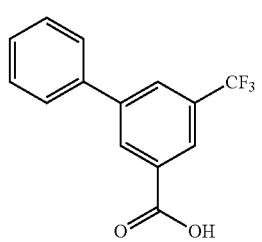
14-I7
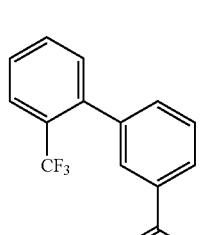
14-I8
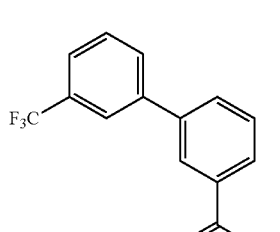
14-I9
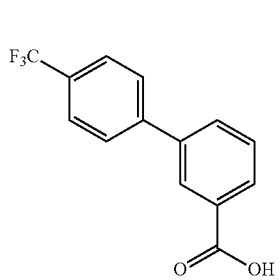
14-I10
14-I11
14-I12
14-I13
14-I14
14-I15

EXAMPLE 15

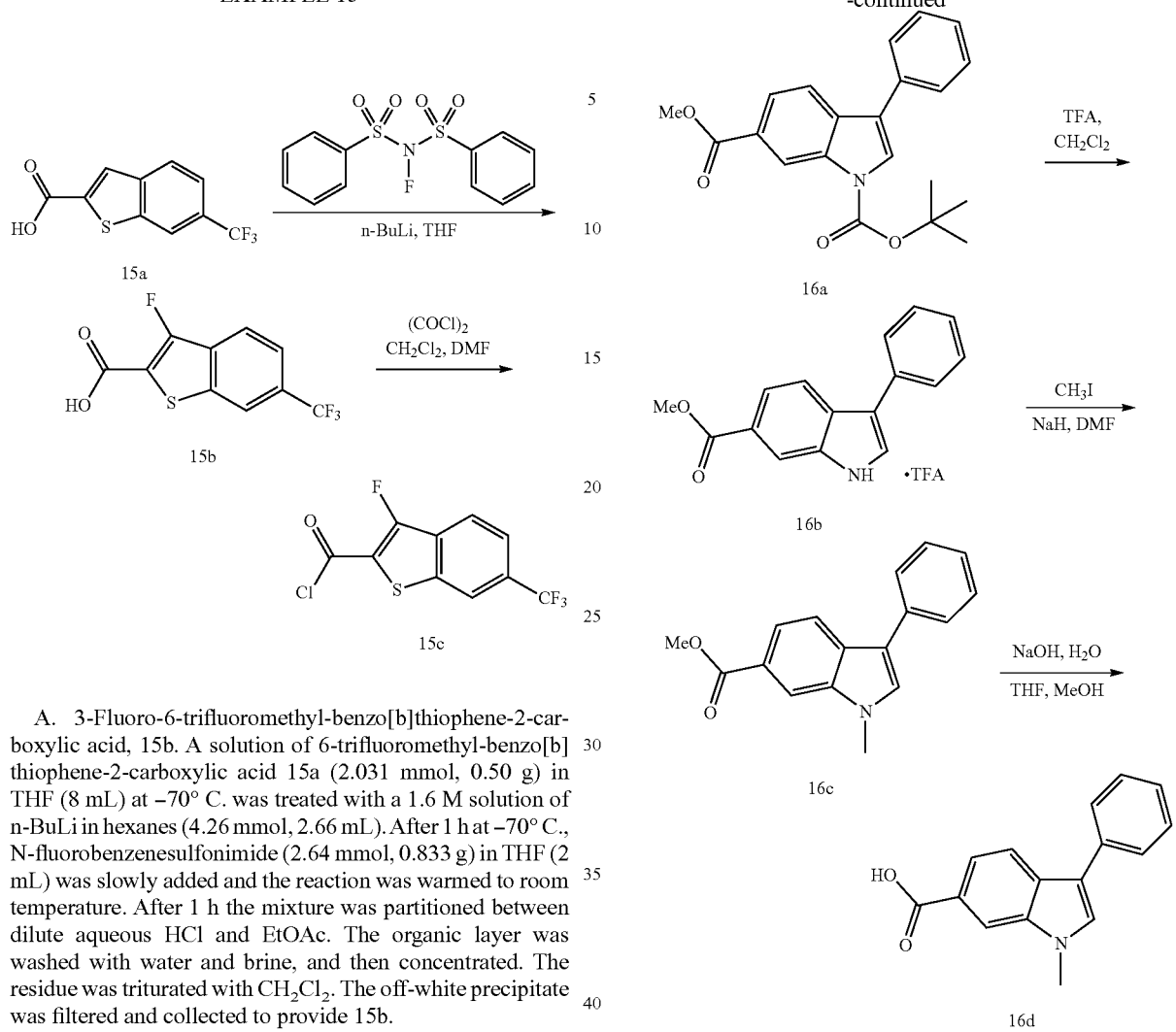

A. 3-Fluoro-6-trifluoromethyl-benzo[b]thiophene-2-carboxylic acid, 15b. A solution of 6-trifluoromethyl-benzo[b]thiophene-2-carboxylic acid 15a (2.031 mmol, 0.50 g) in THF (8 mL) at −70° C. was treated with a 1.6 M solution of n-BuLi in hexanes (4.26 mmol, 2.66 mL). After 1 h at −70° C., N-fluorobenzenesulfonimide (2.64 mmol, 0.833 g) in THF (2 mL) was slowly added and the reaction was warmed to room temperature. After 1 h the mixture was partitioned between dilute aqueous HCl and EtOAc. The organic layer was washed with water and brine, and then concentrated. The residue was triturated with $CH_2Cl_2$. The off-white precipitate was filtered and collected to provide 15b.

B. 3-Fluoro-6-trifluoromethyl-benzo[b]thiophene-2-carbonyl chloride, 15c. To compound 15b (0.14 g, 0.53 mmol) in $CH_2Cl_2$ (5 mL) at room temperature was added $(COCl)_2$ (0.051 mL, 0.58 mmol), followed by 2 drops of DMF. The reaction mixture was stirred at room temperature for 18 h. The reaction mixture was then concentrated to give compound 15c.

EXAMPLE 16

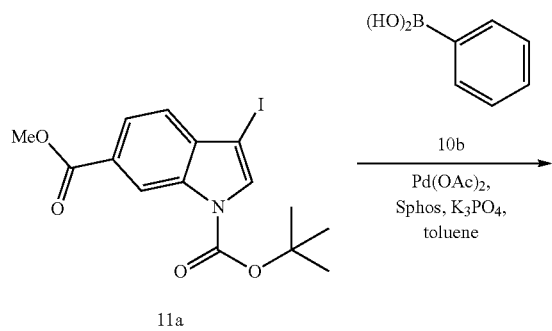

A. 1-tert-Butyl 6-methyl 3-phenyl-1H-indole-1,6-dicarboxylate, 16a. A mixture of 1-tert-butyl 6-methyl 3-iodo-1H-indole-1,6-dicarboxylate 11a (5.02 mmol, 2.016 g), phenylboronic acid 10b (7.53 mmol, 0.92 g), $Pd(OAc)_2$ (0.402 mmol, 90 mg), Sphos 0.904 mmol, (0.37 g), and $K_3PO_4$ (10.1 mmol, 2.13 g) in toluene (10 mL) in sealed reaction vial was stirred at room temperature for 2 min and then heated at 90° C. under $N_2$ for 4 h. The reaction mixture was quenched with EtOAc and water. The organic layer was concentrated and purified by flash column chromatography (silica gel, 8% EtOAc/hexanes). The desired product was collected as a light yellow solid that was washed with small amount of hexanes to obtain 16a as a white solid.

B. Methyl 3-phenyl-1H-indole-6-carboxylate TFA salt, 16b. To a solution of 1-tert-butyl 6-methyl 3-phenyl-1H-indole-1,6-dicarboxylate 16a (4.04 mmol, 1.42 g) in $CH_2Cl_2$ (8 mL) was added 6 mL of TFA. The resulting solution was stirred for 3 h. The mixture was then concentrated and washed with hexanes to afford 16b.

C. Methyl 1-methyl-3-phenyl-1H-indole-6-carboxylate, 16c. NaH (60% dispersion in mineral oil, 4.52 mmol, 186 mg) was added portion-wise to a solution of methyl 3-phenyl-1H-indole-6-carboxylate TFA salt (2.07 mmol, 757 mg) in DMF at 0° C. and the mixture was stirred for 20 min. Methyl iodide (2.28 mmol, 0.14 mL) was added and the reaction mixture was maintained at 0° C. for 1 h. Water was then added and the reaction was extracted with EtOAc. The organics were concentrated and purified by flash column chromatography (silica gel, 15% EtOAc/hexanes) to give 16c.

D. 1-Methyl-3-phenyl-1H-indole-6-carboxylic acid, 16d. A mixture of compound 16c (517 mg, 1.95 mmol) and LiOH (187 mg, 7.80 mmol) in THF/MeOH/H₂O (4/4/4mL) was stirred for 4 h. A 15% citric acid solution (20 mL) was added, and the mixture was then extracted with EtOAc (3×). The combined extracts were washed with brine, dried over Na₂SO₄, filtered, and concentrated under reduced pressure. The residue, compound 16d, was dried under reduced pressure for 18 h.

Following the procedure described above for Example 16 and substituting the appropriate reagents, starting materials and purification methods known to those skilled in the art, the following intermediate compounds were prepared:

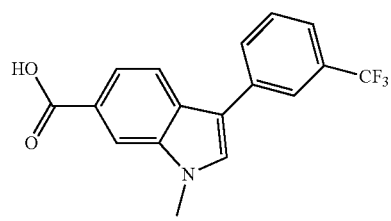

16-I1

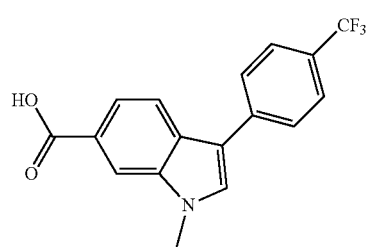

16-I2

EXAMPLE 17

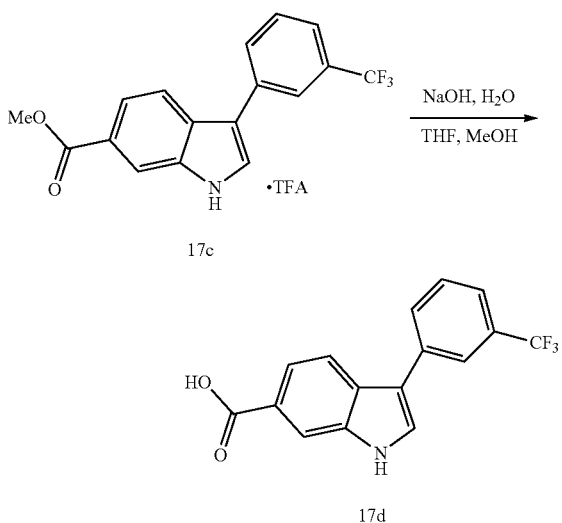

A. 1-tert-Butyl 6-methyl 3-(3-(trifluoromethyl)phenyl)-1H-indole-1,6-dicarboxylate, 17b. The title compound 17b was prepared using the method described in Example 16, substituting 17a for 10b in Step A.

B. Methyl 3-(3-(trifluoromethyl)phenyl)-1H-indole-6-carboxylate TFA salt, 17c. The title compound 17c was prepared using the method described in Example 16, substituting 17b for 16a in Step B.

C. 3-(3-(Trifluoromethyl)phenyl)-1H-indole-6-carboxylic acid, 17d. The title compound was prepared using the method described in Example 16, substituting 17c for 16c in Step D.

Following the procedure described above for Example 17 and substituting the appropriate reagents, starting materials and purification methods known to those skilled in the art, the following intermediate compound was prepared:

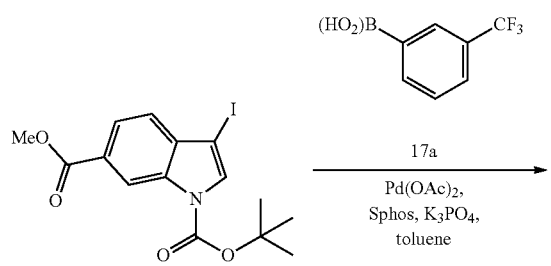

17-I1

EXAMPLE 18

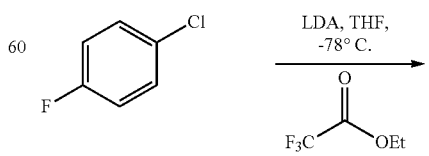

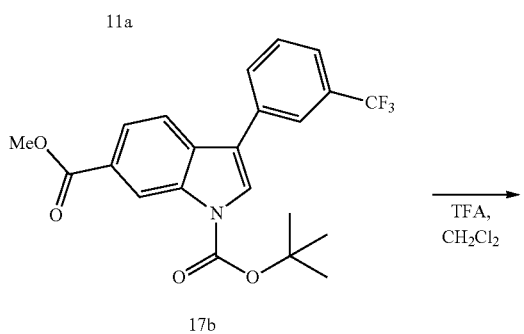

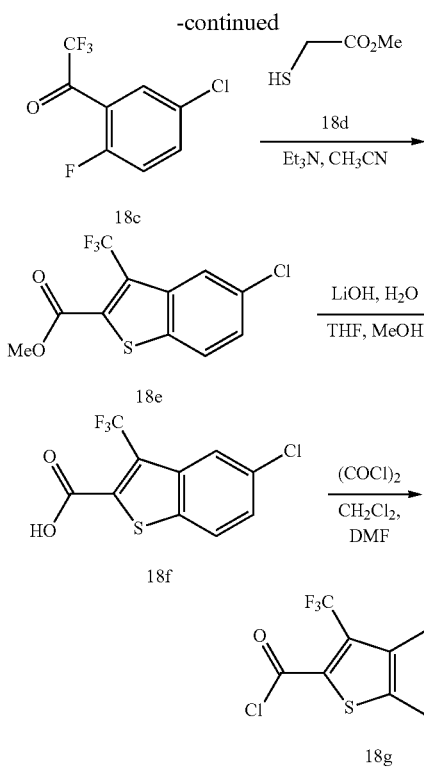

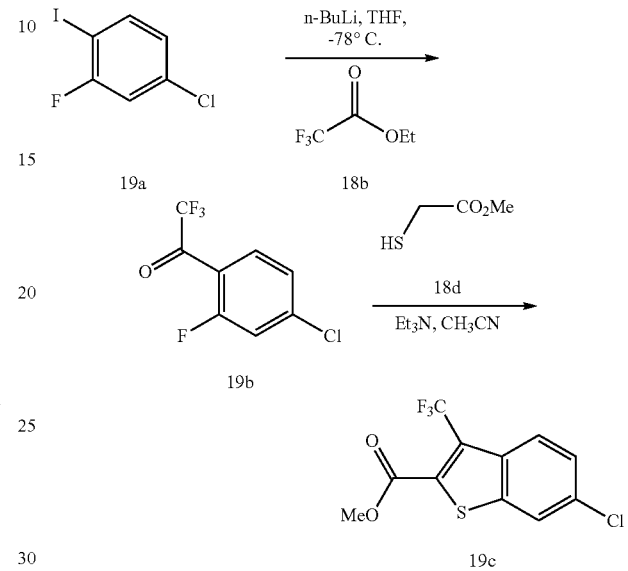

DMF. The reaction mixture was stirred at room temperature for 18 h. The reaction mixture was then concentrated to give compound 18g.

EXAMPLE 19

A. 1-(5-Chloro-2-fluoro-phenyl)-2,2,2-trifluoro-ethanone, 18c. To a solution of LDA (2.0 M in THF/heptane/ethylbenzene, 25.3 mmol, 12.6 mL) in dry THF was slowly added 1-fluoro-4-chloro-bezene 18a (23.0 mmol, 2.45 mL) at −78° C. The mixture was stirred for 1 h at −78° C. and ethyl trifluoroacetate 18b (25.3 mmol, 3.02 mL) was added. The reaction mixture was allowed to warm to room temperature overnight and was quenched with saturated aqueous NH₄Cl solution. The mixture was extracted with EtOAc. The organic extracts were concentrated and purified by flash column chromatography (silica gel, 15% EtOAc/hexanes) to give a mixture of the compound 18c along with a regio-isomeric by-product, 1-(5-fluoro-2-chloro-phenyl)-2,2,2-trifluoroethanone, in a ratio of 5:1 (18c is the major product).

B. Methyl 5-chloro-3-(trifluoromethyl)benzo[b]thiophene-2-carboxylate, 18e. A solution of compound 18c (6.62 mmol, 1.5 g), methyl 2-mercaptoacetate 18d (6.62 mmol, 0.6 mL), and Et₃N (8.6 mmol, 1.2 mL) in acetonitrile (12 mL) was heated at 75° C. for 4 h. The reaction was diluted with EtOAc and water. The organic layer was concentrated and purified by flash column chromatography (silica gel, 10% EtOAc/hexanes) to provide the compound 18e.

C. 5-Chloro-3-trifluoromethyl-benzo[b]thiophene-2-carboxylic acid, 18f. A mixture of compound 18e (574 mg, 1.95 mmol) and LiOH (187 mg, 7.80 mmol) in THF/MeOH/H₂O (4/4/4mL) was stirred for 4 h. A 15% citric acid solution (20 mL) was added, and the mixture was then extracted with EtOAc (3×). The combined extracts were washed with brine, dried over Na₂SO₄, filtered, and concentrated under reduced pressure. The residue, compound 18f, was dried under reduced pressure for 18 h and was used without purification.

D. 5-Chloro-3-trifluoromethyl-benzo[b]thiophene-2-carbonyl chloride, 18g. To compound 18f in CH₂Cl₂ (5 mL) at room temperature was added (COCl)₂, followed by 2 drops of A. 1-(4-Chloro-2-fluoro-phenyl)-2,2,2-trifluoro-ethanone, 19b. To a solution of n-BuLi (1.6 M in hexanes, 4.68 mmol, 2.93 mL) in dry THF was slowly added 4-chloro-2-fluoro-1-iodo-benzene 19a (3.9 mmol, 1.0 g) at −78° C. under N₂. The mixture was stirred for 1 h at −78° C. and ethyl trifluoroacetate 18b (0.51 mL, 4.29 mmol) was added. The reaction was allowed to warm to room temperature overnight and was quenched with saturated aqueous NH₄Cl solution. The mixture was extracted with EtOAc. The organic extracts were concentrated and purified by flash column chromatography (silica gel, 15% EtOAc/hexanes) to give compound 19b.

B. Methyl 6-chloro-3-(trifluoromethyl)benzo[b]thiophene-2-carboxylate, 19c. The title compound 19c was prepared using a similar method described in Example 18, substituting 19b for 18c in Step B.

EXAMPLE 20

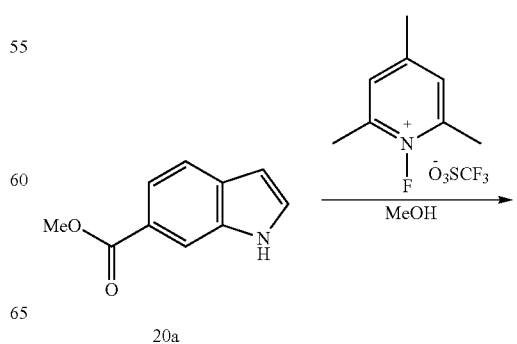

EXAMPLE 21

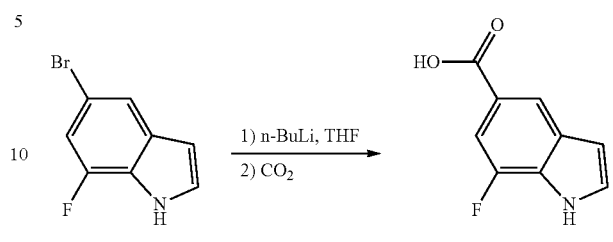

A. 7-Fluoro-1H-indole-5-carboxylic acid, 21b. To a solution of 5-bromo-7-fluoroindole 21a (1.71 mmol, 365 mg) in THF at −60° C. was added n-BuLi (1.6 M solution in hexanes, 5.2 mmol, 3.2 mL). The solution was kept at −60° C. for 4 h and was then poured onto an excess of freshly crushed dry ice. Water was added and the mixture was acidified to pH 4. The organic phase was concentrated and the residue was purified by flash column chromatography (silica gel, 35% EtOAc/hexanes) to give compound 21b.

EXAMPLE 22

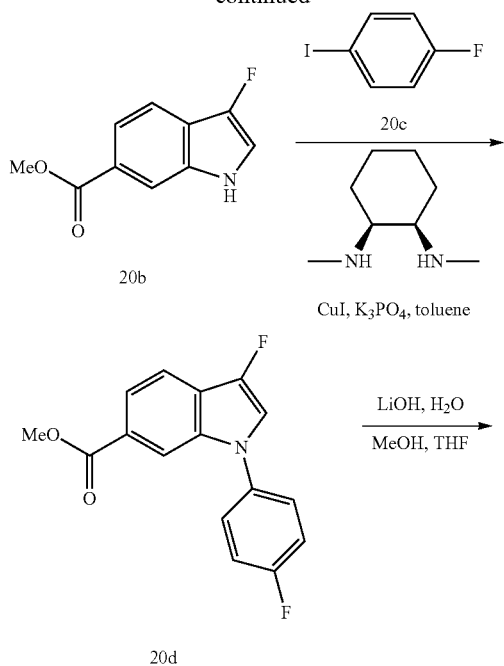

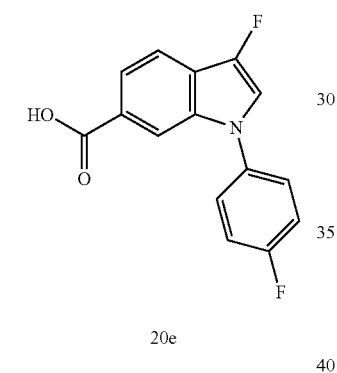

A. Methyl 3-fluoro-1H-indole-6-carboxylate, 20b. A solution of methyl 1H-indole-6-carboxylate 20a (11.4 mmol, 2.0 g) and N-fluoro-2,4,6-trimethylpyridinium triflate (14.8 mmol, 4.3 g) in MeOH (100 mL) was heated at reflux for 18 h. The reaction mixture was concentrated and purified by flash column chromatography (silica gel, 15-20% EtOAc/hexanes) to give compound 20b as an off-white solid.

B. Methyl 3-fluoro-1-(4-fluorophenyl)-1H-indole-6-carboxylate, 20d. Compound 20b (0.264 mmol, 51 mg), CuI (0.0264 mmol, 5 mg) and K$_3$PO$_4$ (0.66 mmol, 40 mg) were combined in a sealed reaction tube and the vial was backflushed with N$_2$. 4-fluoro-iodobezene 20c (0.264 mmol, 0.0394 mL) and N,N'-dimethylcyclohexane-1,2-diamine (0.0792 mmol, 0.0125 mL) were added via syringe, followed by toluene. The reaction mixture was heated at 95° C. for 6 h. The reaction was diluted with EtOAc and water. The reaction mixture was concentrated and purified by flash column chromatography (silica gel, 20% EtOAc/hexanes) to give compound 20d.

C. 3-Fluoro-1-(4-fluorophenyl)-1H-indole-6-carboxylic acid, 20e. The title compound 20e was prepared using the method described in Example 18, Step C.

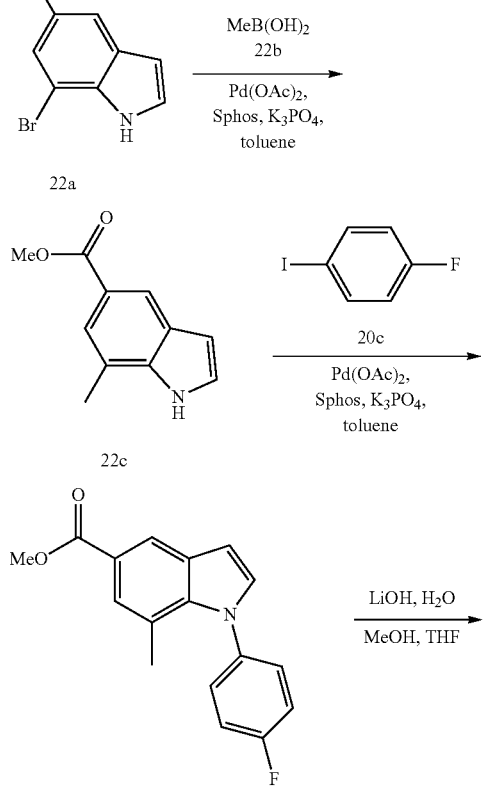

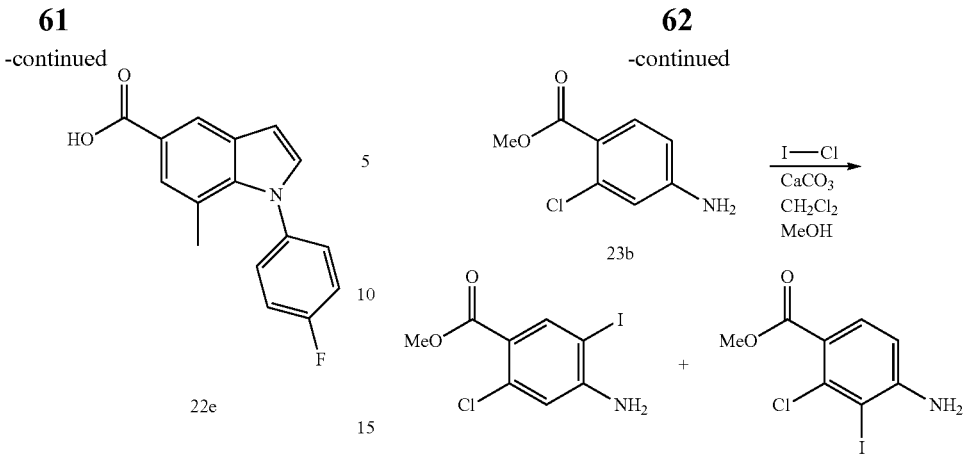

A. Methyl 7-methyl-1H-indole-5-carboxylate, 22c. A mixture of compound 22a (0.613 mmol, 156 mg), methylboronic acid 22b (0.92 mmol, 79 mg), Pd(OAc)₂ (0.09 mmol, 20 mg), SPhos (0.215 mmol, 88 mg), and K₃PO₄ (1.23 mmol, 0.26 g) in toluene (2 mL) was heated to 100° C. for 3 h in a sealed reaction vessel. The reaction was diluted with EtOAc and water. The organic layer was concentrated and purified by flash column chromatography (silica gel, 10% EtOAc/hexanes) to give compound 22c.

B. Methyl 1-(4-fluorophenyl)-7-methyl-1H-indole-5-carboxylate, 22d. The title compound was prepared using the method described in Example 20, substituting 22c for 20b in Step B.

C. 1-(4-Fluorophenyl)-7-methyl-1H-indole-5-carboxylate, 22e. The title compound was prepared using the method described in Example 18, Step C.

Following the procedure described above for Example 22, and substituting the appropriate reagents, starting materials, and purification methods known to those skilled in the art, the following intermediate compound was prepared:

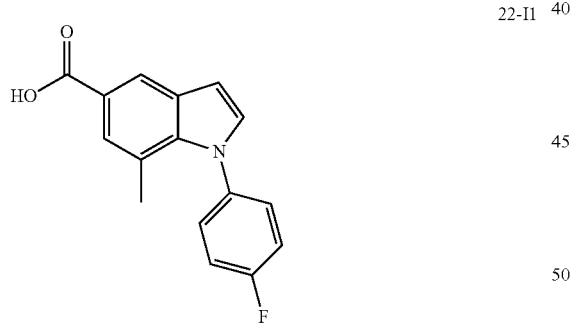

22-I1

EXAMPLE 23

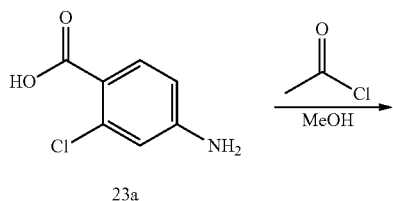

A. Methyl 4-amino-2-chloro-benzoate, 23b. Acetyl chloride (35.2 mmol, 2.5 mL) was added dropwise to a stirring solution of 4-amino-2-chloro-benzoic acid 23a (12.9 mmol, 2.22 g) in methanol (50 mL). The mixture was heated at reflux for 18 h, cooled, and concentrated under vacuum. The residue was taken up in EtOAc, washed with saturated aqueous NaHCO₃ and brine, dried, and concentrated under vacuum. The crude product was purified by flash column chromatography (silica gel, 30% EtOAc/hexanes) to give compound 23b.

B. Methyl 4-amino-2-chloro-5-iodo-benzoate, 23c. To a suspension of compound 23b (1.18 g, 6.38 mmol) and CaCO₃ (12.8 mmol, 1.28 g) in MeOH (13 mL) was added a solution of iodine monchloride (6.70 mmol, 1.09 g) in CH₂Cl₂ (6 mL) dropwise at room temperature. The resulting reaction mixture was stirred at room temperature for 1.5 h. The reaction mixture was concentrated and then partitioned between EtOAc and water. The organic layer was concentrated and purified by flash column chromatography (silica gel, 20-25% EtOAc/hexanes) to provide methyl 4-amino-2-chloro-5-iodo-benzoate 23c as the major the product and methyl 4-amino-2-chloro-3-iodo-benzoate 23d as the minor product.

C. Methyl 4-amino-2-chloro-5-((trimethylsilyl)ethynyl)benzoate, 23e. To a mixture of compound 23c (0.642 mmol, 200 mg), CuI (0.064 mmol, 12.2 mg) and Pd(PPh₃)₂Cl₂ (0.064 mmol, 45 mg) in THF (2 mL) was added ethynyltrimethylsilane (0.963 mmol, 95 mg) followed by Et₃N (7.19 mmol, 1 mL) under N₂. The reaction mixture was stirred at room temperature for 1.5 h and then partitioned between EtOAc and water. The organic layer was concentrated and purified by flash column chromatography (silica gel, 15% EtOAc/hexanes) to give compound 23e.

D. Methyl 6-chloro-1H-indole-5-carboxylate, 23f. A mixture of compound 23e (0.532 mmol, 150 mg) and CuI (0.32 mmol, 60 mg) in DMF (1.5 mL) was heated at 110° C. for 5 h and them cooled to room temperature. The reaction was quenched with water and extracted with EtOAc. The organic layer was concentrated and purified by flash column chromatography (silica gel, 15% EtOAc/hexanes) to give compound 23f.

EXAMPLE 24

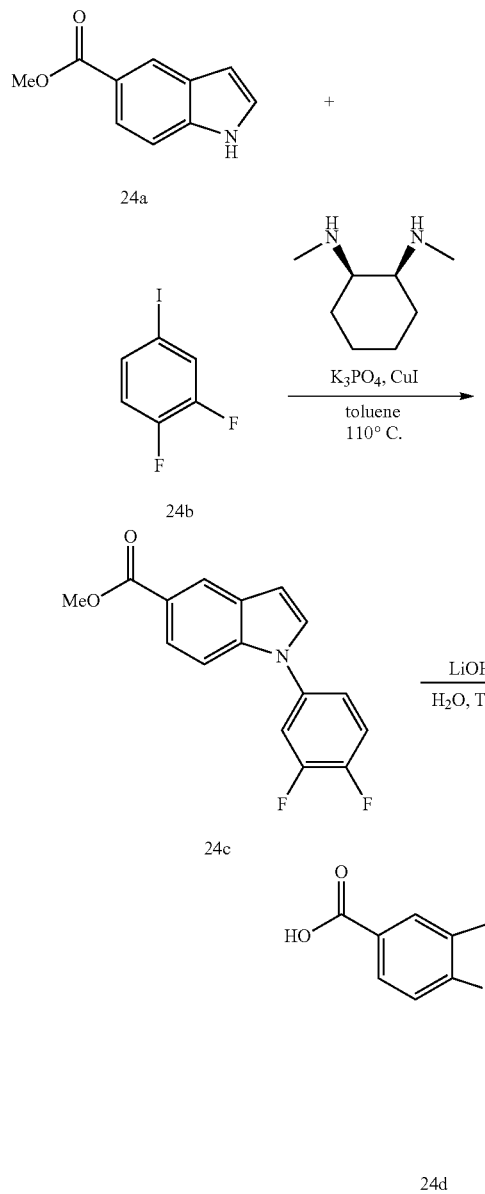

A. Methyl 1-(3,4-difluorophenyl)-indole-5-carboxylate, 24c. A mixture of methyl indole-5-carboxylate 24a (2 g, 11.4 mmol), 1-iodo-3,4-difluoro-benzene 24b (1.5 mL, 12.5 mmol), CuI (0.22 g, 1.14 mmol), trans-N,N'-dimethylcyclohexane-1,2-diamine (0.54 mL, 3.43 mmol), and K₃PO₄ (6.06 g, 28.5 mmol) in toluene (12 mL) was heated at 110° C. for 7 hours. The reaction mixture was diluted with CH₂Cl₂ and filtered. The solution was concentrated and the residue was purified by flash column chromatography (silica gel, 20% EtOAc/heptane) to give 24c (3.0 g).

B. 1-(3,4-difluorophenyl)-indole-5-carboxylic acid, 24d. A mixture of methyl 1-(3,4-difluorophenyl)-indole-5-carboxylate 24c (3.0 g, 10.4 mmol) and LiOH (1.0 g, 41.8 mmol) in THF (120 mL) and H₂O (60 mL) was stirred at room temperature for 5 days. Aqueous 10% HCl solution was added to the reaction mixture to adjust pH=3~4. The resulting mixture was extracted with EtOAc (2×). The organic solution was washed with aq. NaCl, dried over Na₂SO₄ and concentrated to give 24d (2.85 g).

EXAMPLE 25

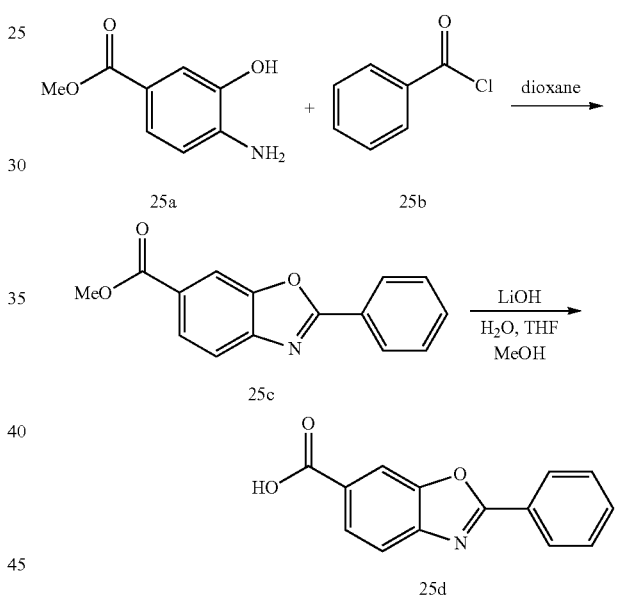

A. Methyl 2-phenyl-benzooxazole-6-carboxylate, 25c. A mixture of methyl 4-amino-3-hydroxy-benzoate 25a (0.3 g, 1.8 mmol) and benzoyl chloride 25b (0.23 mL, 2.0 mmol) in dioxane (2.5 mL) was heated at 210° C. under microwave for 15 min. The reaction mixture was diluted with CH₂Cl₂ and washed with aq. NaHCO₃. The organic solution was dried over Na₂SO₄, concentrated and purified by flash column chromatography (silica gel, 20% EtOAc/heptane) to give 25c (0.39 g).

B. 2-Phenyl-benzooxazole-6-carboxylic acid, 25d. A mixture of methyl 2-phenyl-benzooxazole-6-carboxylate 25c (0.37 g, 1.46 mmol) and LiOH (0.10 g, 4.2 mmol) in THF (4 mL), MeOH (4 mL), and H₂O (4 mL) was stirred at room temperature for 6 h. Aqueous 1N HCl solution was added to the mixture to adjust pH to 3~4. The resulting mixture was extracted with EtOAc (2×). The organic solution was washed with aq. NaCl, dried over Na₂SO₄ and concentrated to give 25d (0.34 g).

EXAMPLE 26

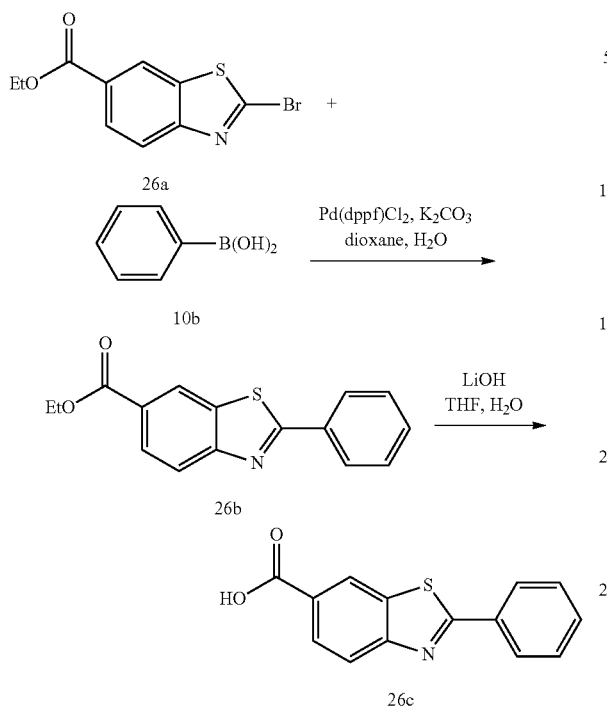

A. Ethyl 2-phenyl-benzothiazole-6-carboxylate, 26b. A mixture of ethyl 2-bromo-benzothiazole-6-carboxylate 26a (300 mg, 1.05 mmol), phenylboronic acid 10b (192 mg, 1.57 mmol), $K_2CO_3$ (188 mg, 1.36 mmol) and Pd(dppf)$Cl_2$·$CH_2Cl_2$ (43 mg, 0.05 mmol) in dioxane (2 mL) and $H_2O$ (0.4 ml) was heated at 120° C. for 25 min under microwave. The reaction mixture was diluted with $CH_2Cl_2$, washed with $H_2O$, dried over $Na_2SO_4$, and concentrated. Purification by flash column chromatography (silica gel, 15% EtOAc/heptane) gave 26b (220 mg).

B. 2-Phenyl-benzothiazole-6-carboxylic acid, 26c. Ethyl 2-phenyl-benzothiazole-6-carboxylate 26b (220 mg, 0.78 mmol) was stirred with LiOH (74 mg, 3.1 mmol) in THF (4 mL) and $H_2O$ (4 mL) for 16 h. Aqueous 1N HCl solution was added to the mixture to adjust pH to 3~4. The resulting mixture was extracted with EtOAc (2×). The organic solution was washed with aq. NaCl, dried over $Na_2SO_4$ and concentrated to give 26c (200 mg).

BIOLOGICAL EXAMPLES

In Vitro Methods

EXAMPLE 1

MGL Enzyme Activity Assay

All rate-based assays were performed in black 384-well polypropylene PCR microplates (Abgene) in a total volume of 30 µL. Substrate 4-methylumbelliferyl butyrate (4MU-B; Sigma) and either purified mutant MGL (mut-MGLL 11-313 L179S L186S) or purified wild type MGL (wt-MGLL 6H-11-313) were diluted separately into 20 mM PIPES buffer (pH=7.0), containing 150 mM NaCl and 0.001% Tween 20. Compounds of Formula (Ia) and (Ib) were pre-dispensed (50 nL) into the assay plate using a Cartesian Hummingbird prior to adding 4MU-B (25 µL of 1.2× solution to a final concentration of 10 µM) followed by enzyme (5 µL of a 6× solution to a final concentration of 5 nM) to initiate the reaction. Final compound concentrations ranged from 17 to 0.0003 µM. The fluorescence change due to 4MU-B cleavage was monitored with excitation and emission wavelengths of 335 and 440 nm, respectively, and a bandwidth of 10 nm (Safire[2], Tecan) at 37° C. for 5 min.

The $IC_{50}$ values for compounds of Formula (Ia) or (Ib) were determined using Excel from a fit of the equation to the concentration-response plot of the fractional activity as a function of inhibitor concentration.

BIOLOGICAL DATA TABLE 1

| Cpd | MGL mutant inh $IC_{50}$ (µM) | MGL wild type inh $IC_{50}$ (µM) |
|---|---|---|
| 1 | 5.2820 | |
| 2 | 4.2403 | |
| 3 | | 0.0060 |
| 4 | | 0.1338 |
| 5 | | 0.0100 |
| 6 | | 0.0290 |
| 7 | | 0.0672 |
| 8 | | 0.1245 |
| 9 | | 7.8469 |
| 10 | | 3.6442 |
| 11 | | <0.005 |
| 12 | | 0.0986 |
| 13 | | 0.9084 |
| 14 | | 0.2254 |
| 15 | | 0.3044 |
| 16 | | 0.0677 |
| 17 | | 0.0554 |
| 18 | | 1.6600 |
| 19 | | <0.005 |
| 20 | | 0.2481 |
| 21 | | <0.005 |
| 22 | | <0.005 |
| 23 | | 0.5675 |
| 24 | | 0.0379 |

EXAMPLE 2

2-AG Accumulation Assay

To measure the accumulation of 2-AG due to inhibition of MGL, one g rat brain was homogenized using a Polytron homogenizer (Brinkmann, PT300) in 10 mL of 20 mM HEPES buffer (pH=7.4), containing 125 mM NaCl, 1 mM EDTA, 5 mM KCl and 20 mM glucose. Compounds of Formula (Ia) or (Ib) (10 µM) were pre-incubated with rat brain homogenate (50 mg). After a 15-min incubation time at 37° C., $CaCl_2$ (final concentration=10 mM) was added and then incubated for 15 min at 37° C. in a total volume of 5 mL. The reactions were stopped with 6 mL organic solvent extraction solution of 2:1 chloroform/methanol. Accumulated 2-AG in the organic phase was measured by a HPLC/MS method, according to the following equation:

percent vehicle=(2-AG accumulation in the presence of compound/2-AG accumulation in vehicle)×100.

BIOLOGICAL DATA TABLE 2

| Cpd | Rat Brain 2AG % VehCntrl (%) @1 µM |
|---|---|
| 3 | 418 |
| 5 | 316 |
| 6 | 302 |
| 7 | 155 |
| 24 | 155 |

EXAMPLE 3

MGL ThermoFluor® Assay—Mutant

The ThermoFluor (TF) assay is a 384-well plate-based binding assay that measures thermal stability of proteins[1,2]. The experiments were carried out using instruments available from Johnson & Johnson Pharmaceutical Research & Development, LLC. TF dye used in all experiments was 1,8-ANS (Invitrogen: A-47). Final TF assay conditions used for MGL studies were 0.07 mg/ml of mutant MGL, 100 µM ANS, 200 mM NaCl, 0.001% Tween-20 in 50 mM PIPES (pH=7.0).

Screening compound plates contained 100% DMSO compound solutions at a single concentration. For follow-up concentration-response studies, compounds were arranged in a pre-dispensed plate (Greiner Bio-one: 781280), wherein compounds were serially diluted in 100% DMSO across 11 columns within a series. Columns 12 and 24 were used as DMSO reference and contained no compound. For both single and multiple compound concentration-repsonse experiments, the compound aliquots (46 nL) were robotically predispensed directly into 384-well black assay plates (Abgene: TF-0384/k) using the Hummingbird liquid handler. Following compound dispension, protein and dye solutions were added to achieve the final assay volume of 3 µL. The assay solutions were overlayed with 1 µL of silicone oil (Fluka, type DC 200: 85411) to prevent evaporation.

Bar-coded assay plates were robotically loaded onto a thermostatically controlled PCR-type thermal block and then heated from 40 to 90° C. degrees at a ramp-rate of 1° C./min for all experiments. Fluorescence was measured by continuous illumination with UV light (Hamamatsu LC6), supplied via fiber optics and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. A single image with 20-sec exposure time was collected at each temperature, and the sum of the pixel intensity in a given area of the assay plate was recorded vs temperature and fit to standard equations to yield the $T_m$[1].

1. Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) *J Biomol Screen* 6, 429-40.
2. Matulis, D., Kranz, J. K., Salemme, F. R., and Todd, M. J. (2005) *Biochemistry* 44, 5258-66.

The $K_d$ values for compounds of Formula (Ia) and (Ib) were determined from a fit of the equation to the concentration-response plot of the fractional activity as a function of $T_m$. For some experiments, quantitative NMR spectroscopy (qNMR) was used to measure concentration of the initial 100% DMSO compound solutions and, using the same fitting method, $qK_d$ values were determined.

BIOLOGICAL DATA TABLE 3

| Cpd | MGL mutant ThermoFluor Kd (µM) | MGL mutant ThermoFluor qKd (µM) (using qNMR conc.) |
| --- | --- | --- |
| 1 | 3.3335 | |
| 2 | 19.6879 | |
| 3 | 0.0398 | |
| 4 | | 0.9430 |
| 5 | | 0.1707 |
| 6 | | 0.6209 |
| 7 | | 0.1863 |
| 8 | | 0.1646 |
| 9 | | 5.6559 |
| 10 | | 10.6316 |
| 11 | 0.0643 | |
| 12 | 0.9940 | |
| 13 | 1.3496 | |
| 14 | 0.4948 | |
| 15 | 1.9706 | |
| 16 | | 1.3804 |
| 17 | | 0.0525 |
| 18 | | 1.3687 |
| 19 | | 0.0008 |
| 20 | | 0.2823 |
| 21 | | 0.0010 |
| 22 | | 0.0025 |
| 23 | 0.7143 | |
| 24 | 0.4334 | |

In Vivo Methods

EXAMPLE 4

CFA-Induced Paw Radiant Heat Hypersensitivity

Each rat may be placed in a test chamber on a warm glass surface and allowed to acclimate for approximately 10 min. A radiant thermal stimulus (beam of light) may be focused through the glass onto the plantar surface of each hind paw in turn. The thermal stimulus may be automatically shut off by a photoelectric relay when the paw is moved or when the cut-off time is reached (20 sec for radiant heat at ~5 amps). An initial (baseline) response latency to the thermal stimulus may be recorded for each animal prior to the injection of complete Freund's adjuvant (CFA). Twenty-four hours following intraplantar CFA injection, the response latency of the animal to the thermal stimulus may be re-evaluated and compared to the animal's baseline response time. Only rats that exhibit at least a 25% reduction in response latency (i.e., are hyperalgesic) are included in further analysis Immediately following the post-CFA latency assessment, the indicated test compound or vehicle may be administered orally. Post-compound treatment withdrawal latencies may be assessed at fixed time intervals, typically 30, 60, 120, 180, and 300 min.

The percent reversal (% R) of hypersensitivity may be calculated in one of two different ways: 1) using group mean values or 2) using individual animal values. More specifically:

Method 1. For all compounds, the % R of hypersensitivity may be calculated using the mean value for groups of animals at each time point according to the following formula:

% reversal=[(group treatment response−group CFA response)/(group baseline response−group CFA response)]×100

Results may be given for the maximum % reversal observed for each compound at any time point tested.

Method 2. For some compounds, the % R of hypersensitivity was calculated separately for each animal according to the following formula:

% reversal=[(individual treatment response−individual CFA response)/(individual baseline response−individual CFA response)]×100.

Results are given as a mean of the maximum % reversal values calculated for each individual animal.

EXAMPLE 5

CFA-Induced Paw Pressure Hypersensitivity

Prior to testing, rats may be acclimated to the handling procedure twice a day for a period of two days. The test consists of placing the left hindpaw on a polytetrafluoroethylene platform and applying a linearly increasing mechanical force (constant rate of 12.5 mmHg/s) in between the third and fourth metatarsal of the dorsum of the rat's hindpaw, with a dome-tipped plinth (0.7 mm in radius), using an analgesymeter (Stoelting, Chicago, Ill.), also known as a Randall-Selitto apparatus. The endpoint may be automatically reached upon hindpaw withdrawal, and the terminal force may be noted (in grams). An initial (baseline) response threshold to the mechanical stimulus may be recorded for each animal prior to the injection of complete Freund's adjuvant (CFA). Forty hours following intraplantar CFA injection, the response threshold of the animal to the mechanical stimulus may be re-evaluated and compared to the animal's baseline response threshold. A response may be defined as a withdrawal of the hindpaw, a struggling to remove the hindpaw or vocalization. Only rats that exhibit at least a 25% reduction in response threshold (i.e., hyperalgesia) may be included in further analysis Immediately following the post-CFA threshold assessment, rats may be administered the indicated test compound or vehicle. Post-treatment withdrawal thresholds may be assessed at 1 h. Paw withdrawal thresholds may be converted to percent reversal of hypersensitivity according to the following formula:

% reversal=[(post treatment response-predose response)/(baseline response-predose response)]×100.

EXAMPLE 6

Chronic Constriction Injury (CCI)-Induced Model of Neuropathic Pain—Cold Acetone-Hypersensitivity Test Male Sprague-Dawley rats (225-450 g) may be used to evaluate the ability of selected compounds to reverse CCI-induced cold hypersensitivity. Four loose ligatures of 4-0 chromic gut may be surgically placed around the left sciatic nerve under inhalation anesthesia as described by Bennett et al. (Bennett G J, Xie Y K. Pain 1988, 33(1): 87-107). Fourteen to 35 days following CCI surgery, subjects may be placed in elevated observation chambers containing wire mesh floors, and five applications of acetone (0.05 mL/application separated by approximately 5 minutes) may be spritzed onto the plantar surface of the paw using a multidose syringe. An abrupt withdrawal or lifting of the paw may be considered a positive response. The number of positive responses may be recorded for each rat over the five trials. Following baseline withdrawal determinations, compounds may be administered in the indicated vehicle, by the indicated route (see Table 6). The number of withdrawals may be re-determined 1 to 4 hr after compound administration. Results may be presented as a percent inhibition of shakes, which may be calculated for each subject as [1-(test compound withdrawals/pre-test withdrawals)]×100 and then averaged by treatment.

EXAMPLE 7

Spinal Nerve Ligation (SNL) Model of Neuropathic Pain—Tactile Allodynia Test For lumbar 5 ($L_5$) spinal nerve ligation (SNL) studies, anesthesia may be induced and maintained on isoflurane inhalation. Fur may be clipped over the dorsal pelvic area, and a 2-cm skin incision may be made just left of midline over the dorsal aspect of the $L_4$-$S_2$ spinal segments, followed by separation of the paraspinal muscles from spinous processes. The transverse process of $L_6$ may be carefully removed, and the $L_5$ spinal nerve may be identified. The left $L_5$ spinal nerve may be ligated tightly with 6-0 silk thread, the muscle may be sutured with 4-0 vicryl, and the skin may be closed with wound clips. Following surgery, s.c. saline (5 mL) may be administered.

Behavioral testing may be performed four weeks post-ligation. Following baseline von Frey determinations to verify the presence of mechanical allodynia, $L_5$ SNL rats may be orally administered the indicated vehicle or drug. Tactile allodynia may be quantified at 30, 60, 100, 180 and 300 min post-dosing by recording the force at which the paw ipsilateral to the nerve ligation is withdrawn from the application of a series of calibrated von Frey filaments (0.4, 0.6, 1.0, 2.0, 4, 6, 8 and 15 g; Stoelting; Wood Dale, Ill.). Beginning at an intermediate stiffness (2.0 g), filaments may be applied to the mid-plantar hind paw for approximately 5 seconds to determine the response threshold, a brisk paw withdrawal leads to the presentation of the next lighter stimulus, whereas a lack of a withdrawal response leads to the presentation of the next stronger stimulus. A total of four responses after the first threshold detection may be collected. The 50% withdrawal thresholds may be interpolated by the method of Dixon as modified by Chaplan et. al., and when response thresholds fall above or below the range of detection, respective values of 15.0 or 0.25 g may be assigned. Threshold data from von Frey filament testing may be reported as withdrawal threshold in grams. Data may be normalized and results may be presented as % MPE (maximum possible effect) of the drug calculated according to the following formula:

$$\% \ MPE = \frac{x \ \text{g/force} - \text{baseline g/force}}{15 \ \text{g/force} - \text{baseline g/force}} \times 100$$

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of Formula (Ia)

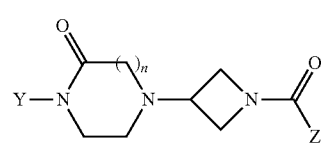

Formula (Ia)

wherein
Y is
i) a $C_{6-10}$ aryl or
ii) a heteroaryl selected from the group consisting of thiazolyl, oxazolyl, pyridinyl, and pyrimidinyl, wherein Y is unsubstituted or substituted with one or two substituents each of which is independently selected from the group consisting of fluoro, chloro, C$_{1-4}$alkyl, C$_{1-4}$alkoxy, cyano, and trifluoromethyl;
Z is selected from the group consisting of
i) a C$_{6-10}$ aryl,
ii) a heteroaryl selected from the group consisting of benzoxazolyl, benzothiazolyl, benzothienyl, indazolyl, and indolyl, or
iii) phenylmethyl-phenyl; wherein the phenyl of phenylmethyl is unsubstituted or substituted with one or two substituents each of which is independently selected from the group consisting of bromo, chloro, fluoro, iodo, C$_{1-4}$alkyl, C$_{1-4}$alkoxy, and trifluoromethyl;
wherein the C$_{6-10}$ aryl and the heteroaryl of Z are unsubstituted or substituted with one or two substitutents each of which is independently selected from the group consisting of bromo, chloro, fluoro, iodo, C$_{1-4}$alkyl, C$_{1-4}$alkoxy, trifluoromethyl, and phenyl,
provided that no more than one substituent of Z is phenyl and said phenyl is unsubstituted or substituted with one or two subsituents each of which is independently selected from the group consisting of trifluoromethyl, chloro, cyano, and fluoro;
n is 1 or 2; and enantiomers, diastereomers, and pharmaceutically acceptable salts thereof.

2. The compound of claim 1 wherein Y is phenyl, thiazolyl, or pyrimidinyl.

3. The compound of claim 2 wherein Y is thiazolyl or pyrimidinyl.

4. The compound of claim 1 wherein
Z is
i) a C$_{6-10}$ aryl or
ii) a heteroaryl selected from the group consisting of benzoxazolyl, benzothiazolyl, benzothienyl, and indolyl,
wherein the C$_{6-10}$ aryl and the heteroaryl of Z are unsubstituted or substituted with one or two substitutents each of which is independently selected from the group consisting of chloro, fluoro, C$_{1-4}$alkyl, trifluoromethyl, and phenyl,
provided that no more than one substituent of Z is phenyl and said phenyl is unsubstituted or substituted with one or two substituents each of which is trifluoromethyl or fluoro.

5. The compound of claim 4 wherein Z is a heteroaryl selected from the group consisting of benzoxazolyl, benzothiazolyl, benzothienyl, and indolyl,
wherein the heteroaryl of Z is unsubstituted or substituted with one or two substitutents each of which is independently selected from the group consisting of chloro, trifluoromethyl, and phenyl,
provided that no more than one substituent of Z is phenyl and said phenyl is unsubstituted or substituted with one or two substituents each of which is trifluoromethyl or fluoro.

6. The compound of claim 1 wherein n is 1.

7. The compound of claim 1 wherein n is 2.

8. A compound of Formula (Ia)

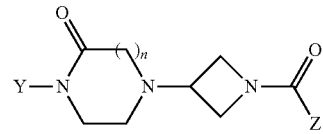

Formula (Ia)

wherein:
Y is
i) phenyl or
ii) a heteroaryl that is thiazolyl or pyrimidinyl;

Z is
i) a C$_{6-10}$ aryl or
ii) a heteroaryl selected from the group consisting of benzoxazolyl, benzothiazolyl, benzothienyl, and indolyl,
wherein the C$_{6-10}$ aryl and the heteroaryl of Z are unsubstituted or substituted with one or two substituents each of which is independently selected from the group consisting of chloro, fluoro, C$_{1-4}$alkyl, trifluoromethyl, and phenyl,
provided that no more than one substituent of Z is phenyl and said phenyl is unsubstituted or substituted with one or two substituents each of which is trifluoromethyl or fluoro;
n is 1 or 2; and enantiomers, diastereomers, and pharmaceutically acceptable salts thereof.

9. The compound of claim 8 wherein n is 1.

10. The compound of claim 8 wherein n is 2.

11. A compound of Formula (Ia)

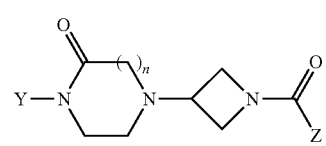

Formula (Ia)

wherein:
Y is thiazolyl or pyrimidinyl;
Z is a heteroaryl selected from the group consisting of benzoxazolyl, benzothiazolyl, benzothienyl, and indolyl,
wherein the heteroaryl of Z is unsubstituted or substituted with one or two substitutents each of which is independently selected from the group consisting of chloro, trifluoromethyl, and phenyl,
provided that no more than one substituent of Z is phenyl, and said phenyl is unsubstituted or substituted with one or two substitutents each of which is trifluoromethyl or fluoro;
n is 1 or 2;
and enantiomers, diastereomers, and pharmaceutically acceptable salts thereof.

12. The compound of claim 11 wherein n is 1.

13. A compound of Formula (Ia)

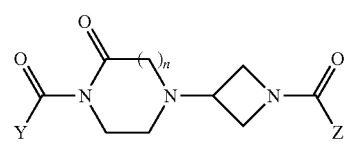

Formula (Ia)

selected from the group consisting of
the compound wherein Y is phenyl, Z is 4-(phenylmethyl)-phenyl, and n is 1;
the compound wherein Y is phenyl, Z is 4-phenyl-phenyl, and n is 1;
the compound wherein Y is pyrimidin-2-yl, Z is 1-(4-trifluoromethyl-phenyl)-1H-indol-5-yl, and n is 1;
the compound wherein Y is pyrimidin-2-yl, Z is 1-(4-fluoro-phenyl)-1H-indol-5-yl, and n is 1;
the compound wherein Y is thiazol-2-yl, Z is 1-(4-fluoro-phenyl)-1H-indol-5-yl, and n is 1;
the compound wherein Y is thiazol-4-yl, Z is 1-(4-fluoro-phenyl)-1H-indol-5-yl, and n is 1;

the compound wherein Y is thiazol-4-yl, Z is 3-chloro-6-trifluoromethyl-benzothien-2-yl, and n is 1;

the compound wherein Y is pyrimidin-2-yl, Z is 3-chloro-6-trifluoromethyl-benzothien-2-yl, and n is 1;

the compound wherein Y is pyrimidin-2-yl, Z is 4-phenyl-phenyl, and n is 1;

the compound wherein Y is pyrimidin-2-yl, Z is 2-phenyl-benzothiazol-6-yl, and n is 1;

the compound wherein Y is thiazol-2-yl, Z is 3-chloro-6-trifluoromethyl-benzothien-2-yl, and n is 1;

the compound wherein Y is thiazol-2-yl, Z is 2-phenyl-benzothiazol-6-yl, and n is 1;

the compound wherein Y is phenyl, Z is 1-(4-trifluoromethyl-phenyl)-1H-indol-5-yl, and n is 1;

the compound wherein Y is phenyl, Z is 3-chloro-6-trifluoromethyl-benzothien-2-yl, and n is 1;

the compound wherein Y is phenyl, Z is 1-(3,4-difluoro-phenyl)-1H-indol-5-yl, and n is 1;

the compound wherein Y is thiazol-2-yl, Z is 2-phenyl-benzoxazol-6-yl, and n is 1;

the compound wherein Y is pyrimidin-2-yl, Z is 3-chloro-6-trifluoromethyl-benzothien-2-yl, and n is 2;

the compound wherein Y is thiazol-2-yl, Z is 4-phenyl-phenyl, and n is 1;

the compound wherein Y is thiazol-2-yl, Z is 3-chloro-6-trifluoromethyl-benzothien-2-yl, and n is 2;

the compound wherein Y is pyrimidin-2-yl, Z is 1-(4-fluoro-phenyl)-1H-indol-5-yl, and n is 2;

the compound wherein Y is thiazol-2-yl, Z is 1-(4-fluoro-phenyl)-1H-indol-5-yl, and n is 2;

the compound wherein Y is thiazol-2-yl, Z is 2-phenyl-benzoxazol-6-yl, and n is 2;

and pharmaceutically acceptable salt forms thereof.

14. A compound of Formula (Ib)

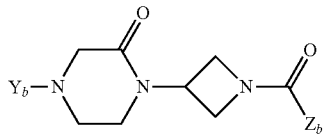

Formula (Ib)

wherein:

$Y_b$ is
i) a $C_{6-10}$ aryl or
ii) a heteroaryl selected from the group consisting of thiazolyl, oxazolyl, pyridinyl, and pyrimidinyl,
wherein $Y_b$ is unsubstituted or substituted with one or two substituents each of which is selected from the group consisting of fluoro, chloro, $C_{1-4}$alkyl, $C_{1-4}$alkoxy, cyano, and trifluoromethyl;

$Z_b$ is
i) a $C_{6-10}$ aryl,
ii) a heteroaryl selected from the group consisting of benzoxazolyl, benzothiazolyl, benzothienyl, and indolyl, or
iii) phenylmethyl-phenyl; wherein the phenyl of phenylmethyl is unsubstituted or substituted with one or two substituents each of which is selected from the group consisting of bromo, chloro, fluoro, iodo, $C_{1-4}$alkyl, $C_{1-4}$alkoxy, and trifluoromethyl,
wherein the $C_{6-10}$ aryl and the heteroaryl of $Z_b$ are unsubstituted or substituted with one or two substitutents each of which is selected from the group consisting of bromo, chloro, fluoro, iodo, $C_{1-4}$alkyl, $C_{1-4}$alkoxy, trifluoromethyl, and phenyl,
provided that no more than one substituent of $Z_b$ is phenyl and said phenyl is unsubstituted or substituted with one or two substituents each of which is selected from the group consisting of trifluoromethyl, chloro, cyano, and fluoro;

and enantiomers, diastereomers, and pharmaceutically acceptable salts thereof.

15. The compound of claim 14 wherein $Y_b$ is thiazolyl or pyrimidinyl.

16. The compound of claim 14 wherein $Z_b$ is the heteroaryl selected from the group consisting of benzoxazolyl, benzothiazolyl, benzothienyl, and indolyl;
wherein the heteroaryl of $Z_b$ is unsubstituted or substituted with one or two substitutents each of which is independently selected from the group consisting of bromo, chloro, fluoro, trifluoromethyl, and phenyl;
provided that no more than one substituent of $Z_b$ is phenyl and said phenyl is unsubstituted or substituted with one or two substituents each of which is trifluoromethyl or fluoro.

17. The compound of claim 16 wherein $Z_b$ is benzothienyl or indolyl,
wherein $Z_b$ is unsubstituted or substituted with one or two substitutents each of which is trifluoromethyl or phenyl,
provided that no more than one substituent of $Z_b$ is phenyl and said phenyl is unsubstituted or substituted with one trifluoromethyl or fluoro substituent.

18. A compound of Formula (Ib)

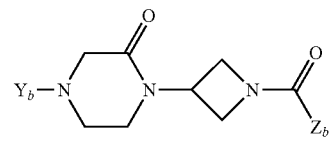

Formula (Ib)

wherein:

$Y_b$ is thiazolyl or pyrimidinyl;
$Z_b$ is a heteroaryl selected from the group consisting of benzoxazolyl, benzothiazolyl, benzothienyl, and indolyl,
wherein the heteroaryl of $Z_b$ is unsubstituted or substituted with one or two substitutents each of which is selected from the group consisting of bromo, chloro, fluoro, trifluoromethyl, and phenyl,
provided that no more than one substituent is phenyl and said phenyl is unsubstituted or substituted with one or two substituents each of which is trifluoromethyl or fluoro;
and enantiomers, diastereomers, and pharmaceutically acceptable salts thereof.

19. A compound of Formula (Ib)

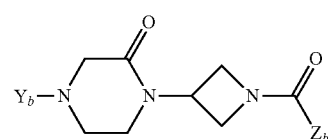

Formula (Ib)

wherein:

$Y_b$ is thiazolyl or pyrimidinyl;
$Z_b$ is benzothienyl or indolyl, wherein $Z_b$ is unsubstituted or substituted with one or two substitutents each of which is trifluoromethyl or phenyl, provided that no more than one substituent of $Z_b$ is phenyl and said phenyl is unsubstituted or substituted with one trifluoromethyl or fluoro substituent;

and enantiomers, diastereomers, and pharmaceutically acceptable salts thereof.

20. A compound of Formula (Ib)

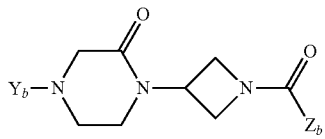

Formula (Ib)

selected from the group consisting of:

the compound wherein $Y_b$ is pyrimidin-2-yl, and $Z_b$ is 6-trifluoromethyl-benzothien-2-yl;

the compound wherein $Y_b$ is pyrimidin-2-yl, and $Z_b$ is 1-(4-trifluoromethyl-phenyl)-1H-indol-5-yl;

and pharmaceutically acceptable salts thereof.

21. A pharmaceutical composition comprising the compound of claim 1 or 13 and a member selected from the group consisting of a pharmaceutically acceptable carrier, a pharmaceutically acceptable excipient, and a pharmaceutically acceptable diluent.

22. A pharmaceutical composition of claim 21, wherein the composition is a solid oral dosage form.

23. A pharmaceutical composition of claim 21, wherein the composition is selected from the group consisting of a syrup, an elixir, and a suspension.

24. A method for treating inflammatory pain in a subject in need thereof comprising administering a therapeutically effective amount of the compound of claim 1 or 13 to the subject.

25. The method of claim 24 wherein the inflammatory pain is due to inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain, pain due to physical trauma, headache, sinus headache, tension headache, or arachnoiditis.

26. A pharmaceutical composition comprising the compound of claim 14 or 20 and a member selected from the group consisting of a pharmaceutically acceptable carrier, a pharmaceutically acceptable excipient, and a pharmaceutically acceptable diluent.

27. A pharmaceutical composition of claim 26, wherein the composition is a solid oral dosage form.

28. A pharmaceutical composition of claim 26, wherein the composition is selected from the group consisting of a syrup, an elixir, and a suspension.

29. A method for treating inflammatory pain in a subject in need thereof comprising administering a therapeutically effective amount of the compound of claim 14 or 20 to the subject.

30. The method of claim 29 wherein the inflammatory pain is due to inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain, pain due to physical trauma, headache, sinus headache, tension headache, or arachnoiditis.

\* \* \* \* \*